(12) United States Patent
Kahle et al.

(10) Patent No.: US 8,357,086 B2
(45) Date of Patent: *Jan. 22, 2013

(54) SURGICAL INSTRUMENT ACCESS DEVICE

(75) Inventors: Henry Kahle, Rancho Santa Margarita, CA (US); Payam Adlparvar, Lake Forest, CA (US); Gary M. Johnson, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/463,161

(22) Filed: May 3, 2012

(65) Prior Publication Data

US 2012/0215070 A1    Aug. 23, 2012

Related U.S. Application Data

(63) Continuation of application No. 11/564,409, filed on Nov. 29, 2006, now Pat. No. 8,187,177, which is a continuation of application No. 10/666,579, filed on Sep. 17, 2003, now Pat. No. 7,163,510.

(51) Int. Cl.
*A61B 1/32* (2006.01)
(52) U.S. Cl. ..................................... 600/208
(58) Field of Classification Search ........... 600/200–234
See application file for complete search history.

(56) References Cited

U.S. PATENT DOCUMENTS

| | | | |
|---|---|---|---|
| 558,364 A | 4/1896 | Doolittle | |
| 1,157,202 A | 10/1915 | Bates et al. | |
| 1,598,284 A | 8/1926 | Kinney | |
| 1,690,995 A | 11/1928 | Pratt | |
| 1,180,466 A | 6/1931 | Deutsch | |
| 1,810,466 A | * 6/1931 | Deutsch | 128/887 |
| 2,219,564 A | 10/1940 | Reyniers | |
| 2,305,289 A | 12/1942 | Coburg | |
| 2,478,586 A | 8/1949 | Krapp | |
| 2,669,991 A | 2/1954 | Curutchet | |
| 2,695,608 A | 11/1954 | Gibbon | |
| 2,812,758 A | 11/1957 | Blumenschein | |
| 2,835,253 A | 5/1958 | Borgeson | |
| 2,853,075 A | 9/1958 | Hoffman et al. | |

(Continued)

FOREIGN PATENT DOCUMENTS

DE    26 05 148 A1    8/1977

(Continued)

OTHER PUBLICATIONS

U.S. Appl. No. 10/902,756, filed Jul. 29, 2004; Title: Hand Access Port Device, now abandoned.

(Continued)

*Primary Examiner* — Eduardo C Robert
*Assistant Examiner* — Stuart S Bray
(74) *Attorney, Agent, or Firm* — Patrick Y. Ikehara

(57) ABSTRACT

A surgical access device includes a valve that forms a seal with a body wall and provides an access channel into a body cavity. The valve has properties for creating a zero seal in the absence of an instrument as well as an instrument seal for an instrument. The valve can include a gel material and the access channel can include a protective shield to provide for wound protection during insertion and withdrawal of a sharp surgical instrument. The valve further comprises a cap ring which may be inserted or molded with the gel material.

12 Claims, 9 Drawing Sheets

U.S. PATENT DOCUMENTS

| | | | |
|---|---|---|---|
| 3,039,468 A | 6/1962 | Price | |
| 3,057,350 A | 10/1962 | Cowley | |
| 3,111,943 A * | 11/1963 | Orndorff | 128/850 |
| 3,195,934 A | 7/1965 | Parrish | |
| 3,244,169 A | 4/1966 | Baxter | |
| 3,253,594 A | 5/1966 | Matthews et al. | |
| 3,313,299 A * | 4/1967 | Spademan | 604/167.02 |
| 3,329,390 A | 7/1967 | Hulsey | |
| 3,332,417 A * | 7/1967 | Blanford et al. | 128/850 |
| 3,347,226 A * | 10/1967 | Harrower | 128/850 |
| 3,347,227 A * | 10/1967 | Harrower | 128/850 |
| 3,397,692 A | 8/1968 | Creager, Jr. et al. | |
| 3,402,710 A | 9/1968 | Paleschuck | |
| 3,416,520 A | 12/1968 | Creager, Jr. | |
| 3,447,533 A | 6/1969 | Spicer | |
| 3,522,800 A | 8/1970 | Lesser | |
| 3,523,534 A | 8/1970 | Nolan | |
| 3,570,475 A | 3/1971 | Weinstein | |
| 3,656,485 A | 4/1972 | Robertson | |
| 3,685,786 A | 8/1972 | Woodson | |
| 3,717,151 A | 2/1973 | Collett | |
| 3,717,883 A | 2/1973 | Mosher | |
| 3,729,006 A | 4/1973 | Wilder et al. | |
| 3,782,370 A * | 1/1974 | McDonald | 600/207 |
| 3,797,478 A | 3/1974 | Walsh et al. | |
| 3,799,166 A | 3/1974 | Marsan | |
| 3,807,393 A | 4/1974 | McDonald | |
| 3,828,764 A | 8/1974 | Jones | |
| 3,831,583 A | 8/1974 | Edmunds et al. | |
| 3,841,332 A | 10/1974 | Treacle | |
| 3,850,172 A | 11/1974 | Cazalis | |
| 3,853,126 A | 12/1974 | Schulte | |
| 3,853,127 A | 12/1974 | Spademan | |
| 3,856,021 A | 12/1974 | McIntosh | |
| 3,860,274 A | 1/1975 | Ledstrom et al. | |
| 3,861,416 A | 1/1975 | Wichterle | |
| 3,907,389 A | 9/1975 | Cox et al. | |
| 3,915,171 A | 10/1975 | Shermeta | |
| 3,965,890 A | 6/1976 | Gauthier | |
| 3,970,089 A | 7/1976 | Saice | |
| 3,996,623 A | 12/1976 | Kaster | |
| 4,000,739 A | 1/1977 | Stevens | |
| 4,016,884 A | 4/1977 | Kwan-Gett | |
| 4,024,872 A | 5/1977 | Muldoon | |
| 4,030,500 A | 6/1977 | Ronnquist | |
| 4,043,328 A | 8/1977 | Cawood, Jr. et al. | |
| 4,069,913 A | 1/1978 | Harrigan | |
| 4,082,005 A | 4/1978 | Erdley | |
| 4,083,370 A * | 4/1978 | Taylor | 604/156 |
| 4,096,853 A | 6/1978 | Weigand | |
| 4,112,932 A * | 9/1978 | Chiulli | 604/264 |
| 4,130,113 A | 12/1978 | Graham | |
| 4,177,814 A | 12/1979 | Knepshield et al. | |
| 4,183,357 A * | 1/1980 | Bentley et al. | 604/175 |
| 4,187,849 A | 2/1980 | Stim | |
| 4,188,945 A | 2/1980 | Wenander | |
| 4,217,664 A | 8/1980 | Faso | |
| 4,222,126 A | 9/1980 | Boretos et al. | |
| 4,228,792 A | 10/1980 | Rhys-Davies | |
| 4,239,036 A | 12/1980 | Krieger | |
| 4,240,411 A * | 12/1980 | Hosono | 600/154 |
| 4,253,201 A | 3/1981 | Ross et al. | |
| 4,254,973 A | 3/1981 | Banjamin | |
| 4,306,562 A | 12/1981 | Osborne | |
| 4,321,915 A | 3/1982 | Leighton | |
| 4,331,138 A | 5/1982 | Jessen | |
| 4,338,934 A | 7/1982 | Spademan | |
| 4,338,937 A | 7/1982 | Lerman | |
| 4,367,728 A | 1/1983 | Mutke | |
| 4,369,284 A | 1/1983 | Chen | |
| 4,399,816 A | 8/1983 | Spangler | |
| 4,402,683 A * | 9/1983 | Kopman | 604/175 |
| 4,411,659 A | 10/1983 | Jensen et al. | |
| 4,421,296 A | 12/1983 | Stephens | |
| 4,424,833 A * | 1/1984 | Spector et al. | 137/849 |
| 4,428,364 A | 1/1984 | Bartolo | |
| 4,430,081 A | 2/1984 | Timmermans | |
| 4,434,791 A * | 3/1984 | Darnell | 600/233 |
| 4,436,519 A | 3/1984 | O'Neill | |
| 4,454,873 A | 6/1984 | Laufenberg et al. | |
| 4,473,067 A | 9/1984 | Schiff | |
| 4,475,548 A | 10/1984 | Muto | |
| 4,485,490 A | 12/1984 | Akers et al. | |
| 4,488,877 A | 12/1984 | Klein | |
| 4,543,088 A | 9/1985 | Bootman et al. | |
| 4,550,713 A | 11/1985 | Hyman | |
| 4,553,537 A | 11/1985 | Rosenberg | |
| 4,555,242 A | 11/1985 | Saudagar | |
| 4,556,996 A | 12/1985 | Wallace | |
| 4,601,710 A | 7/1986 | Moll | |
| 4,610,665 A | 9/1986 | Matsumoto et al. | |
| 4,626,245 A * | 12/1986 | Weinstein | 604/167.04 |
| 4,634,424 A | 1/1987 | O'Boyle | |
| 4,634,432 A | 1/1987 | Kocak | |
| 4,644,951 A | 2/1987 | Bays | |
| 4,649,904 A | 3/1987 | Krauter | |
| 4,653,476 A | 3/1987 | Bonnet | |
| 4,654,030 A | 3/1987 | Moll et al. | |
| 4,655,752 A | 4/1987 | Honkanen et al. | |
| 4,673,393 A | 6/1987 | Suzuki et al. | |
| 4,673,394 A | 6/1987 | Fenton | |
| 4,691,942 A | 9/1987 | Ford | |
| 4,714,749 A | 12/1987 | Hughes et al. | |
| 4,738,666 A | 4/1988 | Fuqua | |
| 4,755,170 A * | 7/1988 | Golden | 604/513 |
| 4,760,933 A | 8/1988 | Christner et al. | |
| 4,776,843 A | 10/1988 | Martinez et al. | |
| 4,777,943 A | 10/1988 | Chvapil | |
| 4,784,646 A | 11/1988 | Feingold | |
| 4,796,629 A | 1/1989 | Grayzel | |
| 4,798,594 A | 1/1989 | Hillstead | |
| 4,802,694 A | 2/1989 | Vargo | |
| 4,808,168 A | 2/1989 | Warring | |
| 4,809,679 A | 3/1989 | Shimonaka et al. | |
| 4,828,554 A | 5/1989 | Griffin | |
| 4,842,931 A | 6/1989 | Zook | |
| 4,848,575 A | 7/1989 | Nakamura et al. | |
| 4,856,502 A * | 8/1989 | Ersfeld et al. | 602/8 |
| 4,863,430 A | 9/1989 | Klyce et al. | |
| 4,863,438 A * | 9/1989 | Gauderer et al. | 604/247 |
| 4,889,107 A | 12/1989 | Kaufman | |
| 4,895,565 A | 1/1990 | Hillstead | |
| 4,897,081 A | 1/1990 | Poirier | |
| 4,903,710 A | 2/1990 | Jessamine et al. | |
| 4,911,974 A * | 3/1990 | Shimizu et al. | 428/143 |
| 4,915,132 A | 4/1990 | Hodge et al. | |
| 4,926,882 A | 5/1990 | Lawrence | |
| 4,929,235 A | 5/1990 | Merry et al. | |
| 4,944,732 A | 7/1990 | Russo | |
| 4,950,222 A | 8/1990 | Scott et al. | |
| 4,950,223 A * | 8/1990 | Silvanov | 600/32 |
| 4,984,564 A * | 1/1991 | Yuen | 600/207 |
| 4,991,593 A * | 2/1991 | LeVahn | 128/856 |
| 4,998,538 A | 3/1991 | Charowsky et al. | |
| 5,000,745 A | 3/1991 | Guest et al. | |
| 5,009,224 A | 4/1991 | Cole | |
| 5,015,228 A | 5/1991 | Columbus et al. | |
| 5,019,101 A | 5/1991 | Purkait et al. | |
| 5,026,366 A | 6/1991 | Leckrone | |
| 5,037,379 A | 8/1991 | Clayman et al. | |
| 5,041,095 A | 8/1991 | Littrell | |
| 5,045,070 A | 9/1991 | Grodecki et al. | |
| D320,658 S | 10/1991 | Quigley et al. | |
| 5,071,411 A | 12/1991 | Hillstead | |
| 5,073,169 A | 12/1991 | Raiken | |
| 5,074,878 A | 12/1991 | Bark et al. | |
| 5,082,005 A | 1/1992 | Kaldany | |
| 5,086,763 A | 2/1992 | Hathman | |
| 5,092,846 A | 3/1992 | Nishijima et al. | |
| 5,104,389 A | 4/1992 | Deem | |
| 5,125,396 A | 6/1992 | Ray | |
| 5,125,897 A | 6/1992 | Quinn et al. | |
| 5,127,626 A | 7/1992 | Hilal et al. | |
| 5,129,885 A | 7/1992 | Green et al. | |
| 5,141,498 A | 8/1992 | Christian | |
| 5,149,327 A | 9/1992 | Oshiyama | |
| 5,156,617 A | 10/1992 | Reid | |

| Patent No. | Date | Inventor(s) |
|---|---|---|
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Rirchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,409 A | 9/1993 | Buelna |
| 5,242,412 A | 9/1993 | Blake, III |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A * | 8/1994 | Rowe et al. ............ 604/167.06 |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A * | 11/1994 | Brinkerhoff et al. ........ 606/213 |
| 5,368,545 A * | 11/1994 | Schaller et al. ............. 600/37 |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A * | 2/1995 | Hildwein et al. ............ 604/174 |
| 5,395,367 A | 3/1995 | Wilk |
| 5,403,264 A | 4/1995 | Wohlers et al. |
| 5,403,336 A | 4/1995 | Kieturakis et al. |
| 5,407,433 A * | 4/1995 | Loomas .................. 604/167.06 |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Dubrul et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A * | 1/1996 | Cuschieri et al. ............ 606/213 |
| 5,486,426 A | 1/1996 | McGee et al. |
| 5,490,843 A | 2/1996 | Hildwein et al. |
| 5,492,304 A | 2/1996 | Smith et al. |
| 5,496,280 A * | 3/1996 | Vandenbroek et al. .. 604/167.03 |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |
| 5,514,133 A * | 5/1996 | Golub et al. .................... 606/1 |
| 5,514,153 A | 5/1996 | Bonutti |
| 5,518,278 A | 5/1996 | Sampson |
| 5,520,632 A | 5/1996 | Leveen |
| 5,522,791 A * | 6/1996 | Leyva ............................ 600/207 |
| 5,522,824 A | 6/1996 | Ashby |
| 5,524,644 A * | 6/1996 | Crook ............................ 128/888 |
| 5,526,536 A * | 6/1996 | Cartmill ......................... 2/161.7 |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A * | 8/1996 | Danks et al. .................. 604/256 |
| 5,545,179 A * | 8/1996 | Williamson, IV ............ 606/213 |
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A * | 2/1997 | Smith et al. .................. 604/256 |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A * | 6/1997 | Mollenauer et al. .......... 606/213 |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |
| 5,657,963 A | 8/1997 | Hinchliffe et al. |
| 5,658,272 A | 8/1997 | Hasson |
| 5,658,306 A | 8/1997 | Kieturakis |

| | | | |
|---|---|---|---|
| 5,662,615 A | 9/1997 | Blake, III | |
| 5,672,168 A | 9/1997 | de la Torre et al. | |
| 5,681,341 A | 10/1997 | Lunsford et al. | |
| 5,683,378 A | 11/1997 | Christy | |
| 5,685,854 A | 11/1997 | Green et al. | |
| 5,685,857 A | 11/1997 | Negus et al. | |
| 5,697,914 A | 12/1997 | Brimhall | |
| 5,707,703 A | 1/1998 | Rothrum et al. | |
| 5,709,664 A | 1/1998 | Vandenbroek et al. | |
| 5,713,858 A | 2/1998 | Heruth et al. | |
| 5,713,869 A | 2/1998 | Morejon | |
| 5,720,730 A | 2/1998 | Blake, III | |
| 5,725,536 A | 3/1998 | Oberlin et al. | |
| 5,728,103 A | 3/1998 | Picha et al. | |
| 5,730,748 A | 3/1998 | Fogarty et al. | |
| 5,735,791 A | 4/1998 | Alexander et al. | |
| 5,738,628 A | 4/1998 | Sierocuk et al. | |
| 5,741,234 A | 4/1998 | Aboul-Hosn | |
| 5,741,298 A * | 4/1998 | MacLeod | 606/213 |
| 5,743,884 A | 4/1998 | Hasson et al. | |
| 5,749,882 A | 5/1998 | Hart et al. | |
| 5,755,660 A | 5/1998 | Tyagi | |
| 5,760,117 A | 6/1998 | Chen | |
| 5,769,783 A | 6/1998 | Fowler | |
| 5,782,812 A | 7/1998 | Hart et al. | |
| 5,782,817 A * | 7/1998 | Franzel et al. | 604/256 |
| 5,782,859 A | 7/1998 | Nicholas et al. | |
| 5,788,676 A | 8/1998 | Yoon | |
| 5,792,119 A * | 8/1998 | Marx | 604/247 |
| 5,795,290 A | 8/1998 | Bridges | |
| 5,803,919 A | 9/1998 | Hart et al. | |
| 5,803,921 A | 9/1998 | Bonadio | |
| 5,803,923 A | 9/1998 | Singh-Derewa et al. | |
| 5,807,350 A | 9/1998 | Diaz | |
| 5,810,712 A | 9/1998 | Dunn | |
| 5,810,721 A | 9/1998 | Mueller et al. | |
| 5,813,409 A | 9/1998 | Leahy et al. | |
| 5,814,026 A | 9/1998 | Yoon | |
| 5,817,062 A | 10/1998 | Flom et al. | |
| 5,819,375 A | 10/1998 | Kastner | |
| 5,820,555 A | 10/1998 | Watkins, III et al. | |
| 5,820,600 A | 10/1998 | Carlson et al. | |
| 5,830,191 A | 11/1998 | Hildwein et al. | |
| 5,832,925 A | 11/1998 | Rothrum | |
| 5,836,871 A | 11/1998 | Wallace et al. | |
| 5,841,298 A | 11/1998 | Huang | |
| 5,842,971 A | 12/1998 | Yoon | |
| 5,848,992 A | 12/1998 | Hart et al. | |
| 5,853,395 A * | 12/1998 | Crook et al. | 604/174 |
| 5,853,417 A | 12/1998 | Fogarty et al. | |
| 5,857,461 A | 1/1999 | Levitsky et al. | |
| 5,860,995 A | 1/1999 | Berkelaar | |
| 5,865,728 A | 2/1999 | Moll et al. | |
| 5,865,729 A | 2/1999 | Meehan et al. | |
| 5,865,807 A * | 2/1999 | Blake, III | 604/167.06 |
| 5,865,817 A | 2/1999 | Moenning et al. | |
| 5,871,474 A | 2/1999 | Hermann et al. | |
| 5,876,413 A | 3/1999 | Fogarty et al. | |
| 5,879,368 A | 3/1999 | Hoskin et al. | |
| 5,882,344 A | 3/1999 | Stouder, Jr. | |
| 5,884,639 A | 3/1999 | Chen | |
| 5,894,843 A | 4/1999 | Benetti et al. | |
| 5,895,377 A * | 4/1999 | Smith et al. | 604/256 |
| 5,899,208 A * | 5/1999 | Bonadio | 128/897 |
| 5,899,913 A | 5/1999 | Fogarty et al. | |
| 5,904,703 A | 5/1999 | Gilson | |
| 5,906,577 A * | 5/1999 | Beane et al. | 600/207 |
| 5,913,847 A | 6/1999 | Yoon | |
| 5,916,198 A | 6/1999 | Dillow | |
| 5,916,232 A | 6/1999 | Hart | |
| 5,919,476 A | 7/1999 | Fischer et al. | |
| 5,931,832 A | 8/1999 | Jensen | |
| 5,947,922 A * | 9/1999 | MacLeod | 604/27 |
| 5,951,467 A | 9/1999 | Picha et al. | |
| 5,951,588 A | 9/1999 | Moenning | |
| 5,957,888 A | 9/1999 | Hinchliffe et al. | |
| 5,957,913 A | 9/1999 | de la Torre et al. | |
| 5,962,572 A | 10/1999 | Chen | |
| 5,964,781 A * | 10/1999 | Mollenauer et al. | 606/213 |
| 5,976,174 A | 11/1999 | Ruiz | |
| 5,989,232 A | 11/1999 | Yoon | |
| 5,989,233 A | 11/1999 | Yoon | |
| 5,989,266 A | 11/1999 | Foster | |
| 5,993,471 A | 11/1999 | Riza et al. | |
| 5,993,485 A | 11/1999 | Beckers | |
| 5,994,450 A | 11/1999 | Pearce | |
| 5,997,515 A | 12/1999 | de la Torre et al. | |
| 6,004,303 A | 12/1999 | Peterson | |
| 6,010,494 A * | 1/2000 | Schafer et al. | 604/533 |
| 6,017,355 A | 1/2000 | Hessel et al. | |
| 6,018,094 A | 1/2000 | Fox | |
| 6,024,736 A | 2/2000 | de la Torre et al. | |
| 6,025,067 A | 2/2000 | Fay | |
| 6,033,426 A * | 3/2000 | Kaji | 606/213 |
| 6,033,428 A * | 3/2000 | Sardella | 606/213 |
| 6,035,559 A | 3/2000 | Freed et al. | |
| 6,042,573 A | 3/2000 | Lucey | |
| 6,045,535 A * | 4/2000 | Ben Nun | 604/167.01 |
| 6,048,309 A | 4/2000 | Flom et al. | |
| 6,050,871 A | 4/2000 | Chen | |
| 6,053,934 A | 4/2000 | Andrews et al. | |
| 6,059,816 A | 5/2000 | Moenning | |
| 6,066,117 A | 5/2000 | Fox et al. | |
| 6,068,639 A | 5/2000 | Fogarty et al. | |
| 6,077,288 A * | 6/2000 | Shimomura et al. | 606/185 |
| 6,086,603 A | 7/2000 | Termin et al. | |
| 6,090,043 A | 7/2000 | Austin et al. | |
| 6,099,506 A | 8/2000 | Macoviak et al. | |
| 6,110,154 A * | 8/2000 | Shimomura et al. | 604/256 |
| 6,123,689 A | 9/2000 | To | |
| 6,142,935 A * | 11/2000 | Flom et al. | 600/206 |
| 6,142,936 A * | 11/2000 | Beane et al. | 600/207 |
| 6,149,642 A * | 11/2000 | Gerhart et al. | 606/1 |
| 6,150,608 A * | 11/2000 | Wambeke et al. | 174/652 |
| 6,159,182 A | 12/2000 | Davis | |
| 6,162,172 A * | 12/2000 | Cosgrove et al. | 600/208 |
| 6,162,196 A | 12/2000 | Hart et al. | |
| 6,162,206 A | 12/2000 | Bindokas | |
| 6,163,949 A | 12/2000 | Neuenschwander | |
| 6,164,279 A | 12/2000 | Tweedle | |
| 6,171,282 B1 * | 1/2001 | Ragsdale | 604/171 |
| 6,183,486 B1 | 2/2001 | Snow et al. | |
| 6,197,002 B1 | 3/2001 | Peterson | |
| 6,217,555 B1 | 4/2001 | Hart et al. | |
| 6,217,590 B1 | 4/2001 | Levinson | |
| 6,224,612 B1 | 5/2001 | Bates et al. | |
| 6,228,063 B1 | 5/2001 | Aboul-Hosn | |
| 6,238,373 B1 | 5/2001 | de la Torre et al. | |
| 6,241,768 B1 | 6/2001 | Agarwal et al. | |
| 6,254,533 B1 * | 7/2001 | Fadem et al. | 600/208 |
| 6,254,534 B1 * | 7/2001 | Butler et al. | 600/208 |
| 6,258,065 B1 | 7/2001 | Dennis et al. | |
| 6,264,604 B1 | 7/2001 | Kieturakis et al. | |
| 6,267,751 B1 | 7/2001 | Mangosong | |
| 6,276,661 B1 | 8/2001 | Laird | |
| 6,287,280 B1 | 9/2001 | Lampropoulos et al. | |
| 6,315,770 B1 | 11/2001 | de la Torre et al. | |
| 6,319,246 B1 * | 11/2001 | de la Torre et al. | 606/1 |
| 6,322,541 B2 | 11/2001 | West | |
| 6,325,384 B1 | 12/2001 | Berry, Sr. et al. | |
| 6,346,074 B1 | 2/2002 | Roth | |
| 6,371,968 B1 | 4/2002 | Kogasaka et al. | |
| 6,382,211 B1 * | 5/2002 | Crook | 128/849 |
| 6,383,162 B1 | 5/2002 | Sugarbaker | |
| 6,391,043 B1 | 5/2002 | Moll et al. | |
| 6,413,244 B1 | 7/2002 | Bestetti et al. | |
| 6,413,458 B1 | 7/2002 | Pearce | |
| 6,420,475 B1 | 7/2002 | Chen | |
| 6,423,036 B1 | 7/2002 | Van Huizen | |
| 6,440,061 B1 | 8/2002 | Wenner et al. | |
| 6,440,063 B1 * | 8/2002 | Beane et al. | 600/207 |
| 6,443,957 B1 * | 9/2002 | Addis | 606/108 |
| 6,447,489 B1 * | 9/2002 | Peterson | 604/264 |
| 6,450,983 B1 * | 9/2002 | Rambo | 602/60 |
| 6,454,783 B1 | 9/2002 | Piskun | |
| 6,464,686 B1 | 10/2002 | O'Hara et al. | |
| 6,468,292 B1 | 10/2002 | Mollenauer et al. | |
| 6,482,181 B1 * | 11/2002 | Racenet et al. | 604/167.06 |

| Patent No. | Date | Inventor | Class |
|---|---|---|---|
| 6,485,435 B1 | 11/2002 | Bakal | |
| 6,485,467 B1 | 11/2002 | Crook et al. | |
| 6,488,620 B1 | 12/2002 | Segermark et al. | |
| 6,488,692 B1 | 12/2002 | Spence et al. | |
| 6,494,893 B2 | 12/2002 | Dubrul et al. | |
| 6,527,787 B1 | 3/2003 | Fogarty et al. | |
| 6,533,734 B1 | 3/2003 | Corley, III et al. | |
| 6,551,270 B1 | 4/2003 | Bimbo et al. | |
| 6,551,276 B1 | 4/2003 | Mann et al. | |
| 6,551,344 B2 | 4/2003 | Thill | |
| 6,552,109 B1 | 4/2003 | Chen | |
| 6,554,793 B1 | 4/2003 | Pauker et al. | |
| 6,558,371 B2 | 5/2003 | Dorn | |
| 6,569,120 B1 | 5/2003 | Green | |
| 6,578,577 B2 | 6/2003 | Bonadio et al. | |
| 6,579,281 B2 | 6/2003 | Palmer et al. | |
| 6,582,364 B2 * | 6/2003 | Butler et al. | 600/208 |
| 6,589,167 B1 * | 7/2003 | Shimomura et al. | 600/208 |
| 6,589,211 B1 * | 7/2003 | MacLeod | 604/164.06 |
| 6,607,504 B2 | 8/2003 | Haarala et al. | |
| 6,613,952 B2 * | 9/2003 | Rambo | 602/41 |
| 6,623,426 B2 | 9/2003 | Bonadio et al. | |
| 6,627,275 B1 | 9/2003 | Chen | |
| 6,663,598 B1 * | 12/2003 | Carrillo et al. | 604/167.01 |
| 6,669,674 B1 | 12/2003 | Macoviak et al. | |
| 6,676,639 B1 | 1/2004 | Ternström | |
| 6,702,787 B2 | 3/2004 | Racenet et al. | |
| 6,705,989 B2 | 3/2004 | Cuschieri et al. | |
| 6,706,050 B1 | 3/2004 | Giannadakis | |
| 6,714,298 B2 | 3/2004 | Ryer | |
| 6,716,201 B2 | 4/2004 | Blanco | |
| 6,723,044 B2 * | 4/2004 | Pulford et al. | 600/208 |
| 6,723,088 B2 | 4/2004 | Gaskill, III et al. | |
| 6,725,080 B2 | 4/2004 | Melkent et al. | |
| 6,793,621 B2 | 9/2004 | Butler et al. | |
| 6,794,440 B2 | 9/2004 | Chen | |
| 6,796,940 B2 | 9/2004 | Bonadio et al. | |
| 6,797,765 B2 | 9/2004 | Pearce | |
| 6,800,084 B2 | 10/2004 | Davison et al. | |
| 6,811,546 B1 | 11/2004 | Callas et al. | |
| 6,814,078 B2 * | 11/2004 | Crook | 128/849 |
| 6,814,700 B1 | 11/2004 | Mueller et al. | |
| 6,817,974 B2 | 11/2004 | Cooper et al. | |
| 6,830,578 B2 | 12/2004 | O'Heeron et al. | |
| 6,837,893 B2 | 1/2005 | Miller | |
| 6,840,946 B2 | 1/2005 | Fogarty et al. | |
| 6,840,951 B2 | 1/2005 | de la Torre et al. | |
| 6,846,287 B2 * | 1/2005 | Bonadio et al. | 600/208 |
| 6,860,463 B2 * | 3/2005 | Hartley | 251/4 |
| 6,863,674 B2 | 3/2005 | Kasahara et al. | |
| 6,866,861 B1 | 3/2005 | Luhman | |
| 6,867,253 B1 | 3/2005 | Chen | |
| 6,869,393 B2 | 3/2005 | Butler | |
| 6,878,110 B2 | 4/2005 | Yang et al. | |
| 6,884,253 B1 | 4/2005 | McFarlane | |
| 6,890,295 B2 | 5/2005 | Michels et al. | |
| 6,895,965 B2 | 5/2005 | Scarberry et al. | |
| 6,902,541 B2 * | 6/2005 | McNally et al. | 604/32 |
| 6,902,569 B2 | 6/2005 | Parmer et al. | |
| 6,908,430 B2 * | 6/2005 | Caldwell et al. | 600/207 |
| 6,909,220 B2 | 6/2005 | Chen | |
| 6,913,609 B2 | 7/2005 | Yencho et al. | |
| 6,916,310 B2 | 7/2005 | Sommerich | |
| 6,916,331 B2 | 7/2005 | Mollenauer et al. | |
| 6,929,637 B2 | 8/2005 | Gonzalez et al. | |
| 6,936,037 B2 | 8/2005 | Bubb et al. | |
| 6,939,296 B2 * | 9/2005 | Ewers et al. | 600/206 |
| 6,945,932 B1 * | 9/2005 | Caldwell et al. | 600/208 |
| 6,958,037 B2 * | 10/2005 | Ewers et al. | 600/208 |
| 6,972,026 B1 * | 12/2005 | Caldwell et al. | 606/213 |
| 6,979,324 B2 | 12/2005 | Bybordi et al. | |
| 6,991,602 B2 | 1/2006 | Nakazawa et al. | |
| 6,997,909 B2 * | 2/2006 | Goldberg | 604/175 |
| 7,001,397 B2 | 2/2006 | Davison et al. | |
| 7,008,377 B2 | 3/2006 | Beane et al. | |
| 7,014,628 B2 | 3/2006 | Bousquet | |
| 7,033,319 B2 * | 4/2006 | Pulford et al. | 600/208 |
| 7,052,454 B2 * | 5/2006 | Taylor | 600/114 |
| 7,056,304 B2 | 6/2006 | Bacher et al. | |
| 7,056,321 B2 | 6/2006 | Pagliuca et al. | |
| 7,067,583 B2 | 6/2006 | Chen | |
| 7,077,852 B2 | 7/2006 | Fogarty et al. | |
| 7,081,089 B2 * | 7/2006 | Bonadio et al. | 600/208 |
| 7,083,626 B2 | 8/2006 | Hart et al. | |
| 7,093,599 B2 | 8/2006 | Chen | |
| 7,100,614 B2 | 9/2006 | Stevens et al. | |
| 7,101,353 B2 | 9/2006 | Lui et al. | |
| 7,105,009 B2 | 9/2006 | Johnson | |
| 7,105,607 B2 | 9/2006 | Chen | |
| 7,112,185 B2 | 9/2006 | Hart et al. | |
| 7,118,528 B1 | 10/2006 | Piskun | |
| 7,134,929 B2 | 11/2006 | Chen | |
| 7,153,261 B2 * | 12/2006 | Wenchell | 600/208 |
| 7,163,510 B2 | 1/2007 | Kahle et al. | |
| 7,192,436 B2 | 3/2007 | Sing et al. | |
| 7,193,002 B2 | 3/2007 | Chen | |
| 7,195,590 B2 * | 3/2007 | Butler et al. | 600/207 |
| 7,214,185 B1 | 5/2007 | Rosney et al. | |
| 7,217,277 B2 | 5/2007 | Parihar et al. | |
| 7,222,380 B2 | 5/2007 | Chen | |
| 7,223,257 B2 | 5/2007 | Shubayev et al. | |
| 7,223,278 B2 | 5/2007 | Davison et al. | |
| 7,226,484 B2 * | 6/2007 | Chen | 623/36 |
| 7,235,062 B2 | 6/2007 | Brustad | |
| 7,235,084 B2 | 6/2007 | Skakoon et al. | |
| 7,238,154 B2 | 7/2007 | Ewers et al. | |
| 7,244,244 B2 * | 7/2007 | Racenet et al. | 604/167.06 |
| 7,276,075 B1 | 10/2007 | Callas et al. | |
| 7,290,367 B2 | 11/2007 | Chen | |
| 7,294,103 B2 | 11/2007 | Bertolero et al. | |
| 7,297,106 B2 | 11/2007 | Yamada et al. | |
| 7,300,399 B2 | 11/2007 | Bonadio et al. | |
| 7,316,699 B2 | 1/2008 | McFarlane | |
| 7,331,940 B2 | 2/2008 | Sommerich | |
| 7,338,473 B2 | 3/2008 | Campbell et al. | |
| 7,344,547 B2 | 3/2008 | Piskun | |
| 7,344,568 B2 | 3/2008 | Chen | |
| 7,377,898 B2 * | 5/2008 | Ewers et al. | 600/208 |
| 7,390,317 B2 | 6/2008 | Taylor et al. | |
| 7,393,322 B2 * | 7/2008 | Wenchell | 600/208 |
| 7,412,977 B2 | 8/2008 | Fields et al. | |
| 7,445,597 B2 | 11/2008 | Butler et al. | |
| 7,473,221 B2 | 1/2009 | Ewers et al. | |
| 7,481,765 B2 * | 1/2009 | Ewers et al. | 600/208 |
| 7,537,564 B2 * | 5/2009 | Bonadio et al. | 600/208 |
| 7,540,839 B2 | 6/2009 | Butler et al. | |
| 7,559,893 B2 | 7/2009 | Bonadio et al. | |
| 7,578,832 B2 | 8/2009 | Johnson | |
| 7,645,232 B2 | 1/2010 | Shluzas | |
| 7,650,887 B2 | 1/2010 | Nguyen et al. | |
| 7,661,164 B2 | 2/2010 | Chen | |
| 7,704,207 B2 | 4/2010 | Albrecht et al. | |
| 7,717,847 B2 | 5/2010 | Smith | |
| 7,727,146 B2 * | 6/2010 | Albrecht et al. | 600/208 |
| 7,727,255 B2 | 6/2010 | Taylor et al. | |
| 7,736,306 B2 | 6/2010 | Brustad et al. | |
| 7,749,415 B2 | 7/2010 | Brustad et al. | |
| 7,753,901 B2 | 7/2010 | Piskun et al. | |
| 7,758,500 B2 | 7/2010 | Boyd et al. | |
| 7,766,824 B2 | 8/2010 | Jensen et al. | |
| 7,811,251 B2 | 10/2010 | Wenchell et al. | |
| 7,815,567 B2 * | 10/2010 | Albrecht et al. | 600/208 |
| 7,837,612 B2 | 11/2010 | Gill et al. | |
| 7,850,667 B2 | 12/2010 | Gresham | |
| 7,867,164 B2 | 1/2011 | Butler et al. | |
| 7,878,974 B2 | 2/2011 | Brustad et al. | |
| 7,883,461 B2 | 2/2011 | Albrecht et al. | |
| 7,892,172 B2 | 2/2011 | Albrecht et al. | |
| 7,896,889 B2 | 3/2011 | Mazzocchi et al. | |
| 7,909,760 B2 | 3/2011 | Albrecht et al. | |
| 7,913,697 B2 | 3/2011 | Nguyen et al. | |
| 7,930,782 B2 | 4/2011 | Chen | |
| 8,257,254 B2 * | 9/2012 | Piskun | 600/208 |
| 2001/0037053 A1 * | 11/2001 | Bonadio et al. | 600/208 |
| 2001/0047188 A1 | 11/2001 | Bonadio et al. | |
| 2002/0002324 A1 * | 1/2002 | McManus | 600/208 |
| 2002/0010389 A1 * | 1/2002 | Butler et al. | 600/208 |
| 2002/0013542 A1 | 1/2002 | Bonadio et al. | |

| | | | |
|---|---|---|---|
| 2002/0016607 A1 | 2/2002 | Bonadio et al. | |
| 2002/0026230 A1 | 2/2002 | Moll et al. | |
| 2002/0038077 A1* | 3/2002 | de la Torre et al. | 600/203 |
| 2002/0072762 A1 | 6/2002 | Bonadio et al. | |
| 2002/0111536 A1 | 8/2002 | Cuschieri et al. | |
| 2002/0156432 A1* | 10/2002 | Racenet et al. | 604/256 |
| 2003/0004253 A1 | 1/2003 | Chen | |
| 2003/0028179 A1* | 2/2003 | Piskun | 606/1 |
| 2003/0040711 A1 | 2/2003 | Racenet et al. | |
| 2003/0078478 A1* | 4/2003 | Bonadio et al. | 600/208 |
| 2003/0139756 A1 | 7/2003 | Brustad | |
| 2003/0167040 A1 | 9/2003 | Bacher et al. | |
| 2003/0187376 A1* | 10/2003 | Rambo | 602/42 |
| 2003/0192553 A1* | 10/2003 | Rambo | 128/850 |
| 2003/0225392 A1 | 12/2003 | McMichael et al. | |
| 2003/0236505 A1 | 12/2003 | Bonadio et al. | |
| 2003/0236549 A1 | 12/2003 | Bonadio et al. | |
| 2004/0015185 A1* | 1/2004 | Ewers et al. | 606/213 |
| 2004/0024363 A1 | 2/2004 | Goldberg | |
| 2004/0049099 A1* | 3/2004 | Ewers et al. | 600/206 |
| 2004/0049100 A1* | 3/2004 | Butler et al. | 600/208 |
| 2004/0054353 A1* | 3/2004 | Taylor | 606/1 |
| 2004/0063833 A1 | 4/2004 | Chen | |
| 2004/0068232 A1 | 4/2004 | Hart et al. | |
| 2004/0070187 A1* | 4/2004 | Chen | 280/742 |
| 2004/0072942 A1 | 4/2004 | Chen | |
| 2004/0073090 A1* | 4/2004 | Butler et al. | 600/208 |
| 2004/0092795 A1 | 5/2004 | Bonadio et al. | |
| 2004/0092796 A1* | 5/2004 | Butler et al. | 600/208 |
| 2004/0093018 A1 | 5/2004 | Johnson | |
| 2004/0097793 A1 | 5/2004 | Butler et al. | |
| 2004/0106942 A1 | 6/2004 | Taylor | |
| 2004/0111061 A1 | 6/2004 | Curran | |
| 2004/0127772 A1* | 7/2004 | Ewers et al. | 600/212 |
| 2004/0138529 A1 | 7/2004 | Wiltshire et al. | |
| 2004/0143158 A1 | 7/2004 | Hart et al. | |
| 2004/0154624 A1* | 8/2004 | Bonadio et al. | 128/849 |
| 2004/0167559 A1 | 8/2004 | Taylor et al. | |
| 2004/0173218 A1* | 9/2004 | Yamada et al. | 128/856 |
| 2004/0215063 A1 | 10/2004 | Bonadio et al. | |
| 2004/0230161 A1 | 11/2004 | Zeiner | |
| 2004/0243144 A1 | 12/2004 | Bonadio et al. | |
| 2004/0249248 A1* | 12/2004 | Bonadio et al. | 600/184 |
| 2004/0254426 A1 | 12/2004 | Wenchell | |
| 2004/0260244 A1* | 12/2004 | Piechowicz et al. | 604/167.06 |
| 2004/0267096 A1* | 12/2004 | Caldwell et al. | 600/213 |
| 2005/0020884 A1* | 1/2005 | Hart et al. | 600/206 |
| 2005/0033246 A1 | 2/2005 | Ahlbert et al. | |
| 2005/0059865 A1* | 3/2005 | Kahle et al. | 600/206 |
| 2005/0065475 A1 | 3/2005 | Hart et al. | |
| 2005/0065543 A1 | 3/2005 | Kahle et al. | |
| 2005/0090713 A1 | 4/2005 | Gozales et al. | |
| 2005/0090716 A1* | 4/2005 | Bonadio et al. | 600/207 |
| 2005/0090717 A1* | 4/2005 | Bonadio et al. | 600/208 |
| 2005/0096695 A1 | 5/2005 | Olich | |
| 2005/0131349 A1 | 6/2005 | Albrecht et al. | |
| 2005/0148823 A1 | 7/2005 | Vaugh et al. | |
| 2005/0155611 A1* | 7/2005 | Vaugh et al. | 128/887 |
| 2005/0159647 A1 | 7/2005 | Hart et al. | |
| 2005/0192483 A1* | 9/2005 | Bonadio et al. | 600/208 |
| 2005/0192598 A1 | 9/2005 | Johnson et al. | |
| 2005/0197537 A1* | 9/2005 | Bonadio et al. | 600/208 |
| 2005/0203346 A1 | 9/2005 | Bonadio et al. | |
| 2005/0209510 A1 | 9/2005 | Bonadio et al. | |
| 2005/0222582 A1* | 10/2005 | Wenchell | 606/108 |
| 2005/0240082 A1* | 10/2005 | Bonadio et al. | 600/208 |
| 2005/0241647 A1* | 11/2005 | Nguyen et al. | 128/856 |
| 2005/0251124 A1 | 11/2005 | Zvuloni et al. | |
| 2005/0261720 A1 | 11/2005 | Caldwell et al. | |
| 2005/0267419 A1* | 12/2005 | Smith | 604/256 |
| 2005/0277946 A1 | 12/2005 | Greenhalgh | |
| 2005/0283050 A1 | 12/2005 | Gundlapalli et al. | |
| 2005/0288558 A1* | 12/2005 | Ewers et al. | 600/206 |
| 2005/0288634 A1 | 12/2005 | O'Heeron et al. | |
| 2006/0020164 A1 | 1/2006 | Butler et al. | |
| 2006/0020241 A1 | 1/2006 | Piskun et al. | |
| 2006/0030755 A1* | 2/2006 | Ewers et al. | 600/206 |
| 2006/0041270 A1 | 2/2006 | Lenker | |
| 2006/0047284 A1 | 3/2006 | Gresham | |
| 2006/0047293 A1 | 3/2006 | Haberland et al. | |
| 2006/0052669 A1 | 3/2006 | Hart | |
| 2006/0084842 A1* | 4/2006 | Hart et al. | 600/206 |
| 2006/0106402 A1 | 5/2006 | McLucas | |
| 2006/0129165 A1* | 6/2006 | Edoga et al. | 606/108 |
| 2006/0149137 A1* | 7/2006 | Pingleton et al. | 600/208 |
| 2006/0149306 A1* | 7/2006 | Hart et al. | 606/191 |
| 2006/0161049 A1* | 7/2006 | Beane et al. | 600/207 |
| 2006/0161050 A1* | 7/2006 | Butler et al. | 600/208 |
| 2006/0241651 A1 | 10/2006 | Wilk | |
| 2006/0247498 A1* | 11/2006 | Bonadio et al. | 600/208 |
| 2006/0247499 A1 | 11/2006 | Butler et al. | |
| 2006/0247500 A1 | 11/2006 | Voegele et al. | |
| 2006/0247516 A1 | 11/2006 | Hess et al. | |
| 2006/0247586 A1 | 11/2006 | Voegele et al. | |
| 2006/0247673 A1 | 11/2006 | Voegele et al. | |
| 2006/0247678 A1 | 11/2006 | Weisenburgh, II et al. | |
| 2006/0258899 A1 | 11/2006 | Gill et al. | |
| 2006/0264706 A1 | 11/2006 | Piskun | |
| 2006/0270911 A1 | 11/2006 | Voegele et al. | |
| 2007/0004968 A1 | 1/2007 | Bonadio et al. | |
| 2007/0049966 A1 | 3/2007 | Bonadio et al. | |
| 2007/0093695 A1* | 4/2007 | Bonadio et al. | 600/208 |
| 2007/0118175 A1 | 5/2007 | Butler et al. | |
| 2007/0149859 A1 | 6/2007 | Albrecht | |
| 2007/0151566 A1* | 7/2007 | Kahle et al. | 128/856 |
| 2007/0156023 A1 | 7/2007 | Frasier et al. | |
| 2007/0203398 A1 | 8/2007 | Bonadio et al. | |
| 2007/0208312 A1 | 9/2007 | Norton et al. | |
| 2007/0255219 A1 | 11/2007 | Vaugh et al. | |
| 2007/0299387 A1 | 12/2007 | Williams et al. | |
| 2008/0027476 A1 | 1/2008 | Piskun | |
| 2008/0048011 A1 | 2/2008 | Weller | |
| 2008/0097162 A1* | 4/2008 | Bonadio et al. | 600/208 |
| 2008/0097163 A1* | 4/2008 | Butler et al. | 600/208 |
| 2008/0200767 A1* | 8/2008 | Ewers et al. | 600/208 |
| 2008/0255519 A1 | 10/2008 | Piskun et al. | |
| 2008/0281161 A1 | 11/2008 | Albrecht et al. | |
| 2008/0281162 A1 | 11/2008 | Albrecht et al. | |
| 2009/0012477 A1 | 1/2009 | Norton et al. | |
| 2009/0036745 A1 | 2/2009 | Bonadio et al. | |
| 2009/0069837 A1 | 3/2009 | Bonadio et al. | |
| 2009/0093683 A1 | 4/2009 | Richard et al. | |
| 2009/0093752 A1* | 4/2009 | Richard et al. | 604/24 |
| 2009/0131754 A1* | 5/2009 | Ewers et al. | 600/205 |
| 2009/0137879 A1* | 5/2009 | Ewers et al. | 600/208 |
| 2009/0149714 A1 | 6/2009 | Bonadio | |
| 2009/0182279 A1 | 7/2009 | Wenchell et al. | |
| 2009/0187079 A1* | 7/2009 | Albrecht et al. | 600/206 |
| 2009/0227843 A1 | 9/2009 | Smith et al. | |
| 2009/0292176 A1* | 11/2009 | Bonadio et al. | 600/203 |
| 2009/0326330 A1 | 12/2009 | Bonadio et al. | |
| 2010/0063362 A1 | 3/2010 | Bonadio et al. | |
| 2010/0063364 A1 | 3/2010 | Bonadio et al. | |
| 2010/0081880 A1 | 4/2010 | Widenhouse et al. | |
| 2010/0081881 A1 | 4/2010 | Murray et al. | |
| 2010/0081995 A1 | 4/2010 | Widenhouse et al. | |
| 2010/0100043 A1 | 4/2010 | Racenet | |
| 2010/0113882 A1 | 5/2010 | Widenhouse et al. | |
| 2010/0217087 A1 | 8/2010 | Bonadio et al. | |
| 2010/0228091 A1 | 9/2010 | Widenhouse et al. | |
| 2010/0228092 A1 | 9/2010 | Ortiz et al. | |
| 2010/0228094 A1 | 9/2010 | Ortiz et al. | |
| 2010/0240960 A1 | 9/2010 | Richard | |
| 2010/0249523 A1 | 9/2010 | Spiegel et al. | |
| 2010/0249524 A1 | 9/2010 | Ransden et al. | |
| 2010/0249525 A1 | 9/2010 | Shelton, IV et al. | |
| 2010/0249694 A1 | 9/2010 | Choi et al. | |
| 2010/0261972 A1 | 10/2010 | Widenhouse et al. | |
| 2010/0261975 A1 | 10/2010 | Huey et al. | |
| 2010/0286484 A1 | 11/2010 | Stellon et al. | |
| 2010/0298646 A1 | 11/2010 | Stellon et al. | |
| 2011/0021877 A1 | 1/2011 | Fortier et al. | |
| 2011/0028891 A1 | 2/2011 | Okoniewski | |
| 2011/0034935 A1 | 2/2011 | Kleyman | |
| 2011/0034946 A1 | 2/2011 | Kleyman | |
| 2011/0034947 A1 | 2/2011 | Kleyman | |
| 2011/0071462 A1* | 3/2011 | Ewers et al. | 604/26 |
| 2011/0071463 A1* | 3/2011 | Ewers et al. | 604/26 |

FOREIGN PATENT DOCUMENTS

| | | |
|---|---|---|
| DE | 33 36 279 C2 | 1/1986 |
| DE | 37 39 532 | 12/1988 |
| DE | 37 37 121 | 5/1989 |
| DE | 296 00 939 | 6/1996 |
| DE | 19828009 | 12/1999 |
| EP | 0 113 520 | 7/1984 |
| EP | 0 142 262 | 5/1985 |
| EP | 0 517 248 | 12/1992 |
| EP | 0 537 768 | 4/1993 |
| EP | 0 807 416 | 11/1997 |
| EP | 0 849 517 | 6/1998 |
| EP | 0950376 | 10/1999 |
| EP | 1 118 657 | 7/2001 |
| EP | 1 125 552 | 8/2001 |
| EP | 1 312 318 | 5/2003 |
| EP | 1 407 715 | 4/2004 |
| EP | 2 044 889 | 4/2009 |
| EP | 2 340 792 | 7/2011 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| RU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/26559 | 4/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO 03/034908 | 5/2003 |
| WO | WO 03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2008/015566 | 2/2008 |
| WO | WO 2008/093313 | 8/2008 |
| WO | WO 2008/121294 | 10/2008 |
| WO | WO 2010/082722 | 7/2010 |
| WO | WO 2010/104259 | 9/2010 |

OTHER PUBLICATIONS

U.S. Appl. No. 10/802,125, filed Mar. 15, 2004; Title: Surgical Guide Valve, now abandoned.

U.S. Appl. No. 10/927,551, filed Aug. 25, 2004; Title: Surgical Access System, now abandoned.

U.S. Appl. No. 10/695,295, filed Oct. 28, 2003; Title: Surgical Gel Seal.

U.S. Appl. No. 11/132,741, filed May 18, 2005; Title: Gas-Tight Seal Accomodating Surgical Instruments With a Wide Range of Diameters.

U.S. Appl. No. 11/245,709, filed Oct. 7, 2005; Title: Surgical Access System.

U.S. Appl. No. 11/330,661, filed Jan. 12, 2006; Title: Sealed Surgical Access Device.

U.S. Appl. No. 11/564,409, filed Nov. 29, 2006; Title: Surgical Instrument Access Device.

U.S. Appl. No. 12/108,400, filed Apr. 23, 2008; Title: Wound Retraction Apparatus and Method.

U.S. Appl. No. 12/119,371, filed May 12, 2008; Title: Surgical Retractor With Gel Pad.

U.S. Appl. No. 12/119,414, filed May 12, 2008; Title: Surgical Retractor.

U.S. Appl. No. 12/358,080, filed Jan. 22, 2009; Title: Surgical Instrument Access Device.

U.S. Appl. No. 12/360,634, filed Jan. 27, 2009; Title: Surgical Access Apparatus and Method.

U.S. Appl. No. 12/360,710, filed Jan. 27, 2009; Title: Surgical Access Apparatus and Method.

U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011; Title: Hand Access Laparoscopic Device.
U.S. Appl. No. 13/008,728, filed Jan. 18, 2011; Title: Wound Retractor With Gel Cap.
U.S. Appl. No. 13/023,334, filed Feb. 8, 2011; Title: Circular Surgical Retractor.
U.S. Appl. No. 13/031,892, filed Feb. 22, 2011; Title: Wound Retractor.
U.S. Appl. No. 13/050,042, filed Mar. 17, 2011; Title: Split Hoop Wound Retractor With Gel Pad.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc., dated 1999.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9327, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".
European Patent Office, European Search Report for European Application No. EP 04 00 2889, dated Sep. 13, 2004, entitled "Hand Access Port Device".
European Patent Office, International Search Report and The Written Opinion of the International Searching Authority for International Application No. PCT/US2006/040154, mailed Jan. 30, 2007.
European Patent Office, International Search Report and The Written Opinion of the International Searching Authority for International Application No. PCT/US2006/040073, mailed Jan. 26, 2007.
European Patent Office, International Search Report and The Written Opinion of the International Searching Authority for International Application No. PCT/US2006/039905, mailed Jan. 17, 2007.
European Patent Office, International Search Report and The Written Opinion of the International Searching Authority for International Application No. PCT/US2006/039883, mailed Jan. 31, 2007.
European Patent Office, International Search Report and The Written Opinion of the International Searching Authority for International Application No. PCT/US2006/039800, mailed Apr. 16, 2007.
European Patent Office, International Search Report and The Written Opinion of the International Searching Authority for International Application No. PCT/US2006/039799, mailed Mar. 27, 2007.
European Search Report for corresponding EP 08253236 date of mailing is Feb. 10, 2009 (6 pages).
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484, mailed on Nov. 12, 2004.
International Searching Authority/US, International Search Report and the Written Opinion of the International Searching Authority for International Application No. PCT/US01/29682, mailed on Jun. 14, 2002.
McSweeney, Cannulation of the Rumen in Cattle and Buffaloes, Australian Veterinary Journal, Aug. 1989, vol. 66, No. 8, pp. 266-268.
Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan, dated 1992.
The International Bureau of WIPO, International Preliminary Report on Patentability, dated Aug. 29, 2006, for International Application No. PCT/US2004/028250.
The International Bureau of WIPO, International Preliminary Report on Patentability, dated Apr. 16, 2008, for International Application No. PCT/US2006/039799.
The International Bureau of WIPO, International Preliminary Report on Patentability for International Application No. PCT/US2006/039800 dated Apr. 16, 2008.
Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.

Kagaya, Laparascopic cholecystecomy via two ports, using the "Twin-Port" system, J. Hepatobiliary Pancreat Surg (2001) 8:76-80, dated Feb. 20, 2001.

International Search Report and Written Opinion in PCT/IE2005/000113 mailed on Feb. 22, 2006.

International Search Report and Written Opinion in PCT/IE2007/000050 mailed on Aug. 13, 2007.

Declaration of John R. Brustad dated Dec. 10, 2009, submitted in U.S. Appl. No. 11/548,955, including Appendices A-D regarding product sales brochures and production drawings from 2001 and 2005.

The International Searching Authority, The International Search Report and Written Opinion of the International Searching Authority for International Application No. PCT/US08/63445, mailed Sep. 29, 2008.

The International Searching Authority, The International Search Report and Written Opinion of the International Searching Authority for International Application No. PCT/US08/063463 mailed Sep. 10, 2008.

The International Bureau of WIPO, International Preliminary Report on Patentability for International Application No. PCT/US2008/063463, dated Nov. 17, 2009, entitled "Surgical Retractor".

The International Bureau of WIPO, International Preliminary Report on Patentability for International Application No. PCT/US08/63445, issued Nov. 17, 2009, entitled "Surgical Retractor with Gel Pad".

International Searching Authority—US, International Search Report and Written Opinion of the International Searching Authority for International Application No. PCT/US04/25511, mailed Nov. 7, 2007.

International Bureau of WIPO, International Report on Patentability for International Application No. PCT/US04/25511, mailed Dec. 6, 2007.

European Patent Office, European Search Report for European Patent No. 11172709.5, dated Aug. 16, 2011.

European Patent Office, European Search Report for European Patent No. 11172706.1, dated Aug. 16, 2011.

European Patent Office, European Search Report for European Patent No. 12151288, dated Feb. 10, 2012.

* cited by examiner

SURGICAL INSTRUMENT ACCESS DEVICE

CROSS-REFERENCE TO RELATED APPLICATIONS

This application is a continuation of U.S. patent application Ser. No. 11/564,409, filed on Nov. 29, 2006, which is a continuation of U.S. patent application Ser. No. 10/666,579, filed on Sep. 17, 2003, the disclosures of which are hereby incorporated by reference as if set forth in full herein.

BACKGROUND OF THE INVENTION

1. Field of the Invention

This invention relates generally to devices and other apparatus facilitating sealed access with surgical instruments across a body wall and into a body cavity.

2. Discussion of the Prior Art

In several areas of surgery there exists a need to have mechanisms or devices that can seal a body cavity or space, and yet permit the introduction of surgical instruments of different sizes such as guidewires, endoscopes and staplers. Typical of these areas of surgery is laparoscopic surgery which relies on surgical instruments inserted through the abdominal wall to reach an operative site within the abdominal cavity. In order to increase space around the operative site within the cavity, insufflation gases are typically introduced to inflate the cavity and elevate the abdominal wall. This pressurizing of the abdominal cavity is referred to as pneumoperitoneum. In this context, the need to seal the body cavity or space arises from the need to maintain the pneumoperitoneum even when the instruments are present.

Trocars have been commonly used to provide instrument access in laparoscopic surgeries. These trocars have included elaborate seal structures having zero seals which prevent escape of the gases in the absence of instruments, and instrument seals which prevent escape of the gases in the presence of instruments. Unfortunately, the instrument seals have been able to accommodate only a narrow range of instrument diameters. Where wider ranges were desired multiple seal pairs had to be provided.

Some instruments such as surgical staplers and those having diameters up to about 37 mm have been too large for trocar access. Furthermore, present trocar seals typically require two valves, one for forming an instrument seal in the presence of the instrument, and the other for forming a zero seal in the absence of the instrument. Accordingly, there is a need in the art for a surgical access device that can function both as a zero seal and as an instrument seal, and that can accommodate a wide range of instruments having diameters up to about 37 mm.

SUMMARY OF THE INVENTION

The deficiencies of the prior art are overcome with the present invention which includes a seal apparatus. In one embodiment, the device includes a valve structure formed of a gel including, for example, a thermoplastic base such as KRATON® and an oil. The resulting elastomer has excellent tear strength, high elongation, a very low durometer or hardness, and biocompatibility. The access device can function both as a zero seal and as an instrument seal. Furthermore, it can accommodate a full range of instruments having diameters up to about 37 mm. In another embodiment, several instruments of smaller diameter can be accommodated at the same time with a single access device.

Both tear resistance and sealing capability can be enhanced by encapsulating the gel in a sheath or otherwise providing circumferential reinforcement for the valve structure. Additives can be provided either on or in the gel to enhance properties such as lubricity, appearance, wound treatment and/or protection, anti-cancer protection and anti-microbial protection. Additional chemicals, compounds, pharmaceuticals or even mechanical devices can be mixed with or embedded in the gel material to vary chemical, pharmaceutical or physical properties of the access device.

These and other features and advantages of the invention will be clarified with a description of preferred embodiments and reference to the associated drawings.

DESCRIPTION OF PREFERRED EMBODIMENTS AND BEST MODE OF THE INVENTION

Figure 1:
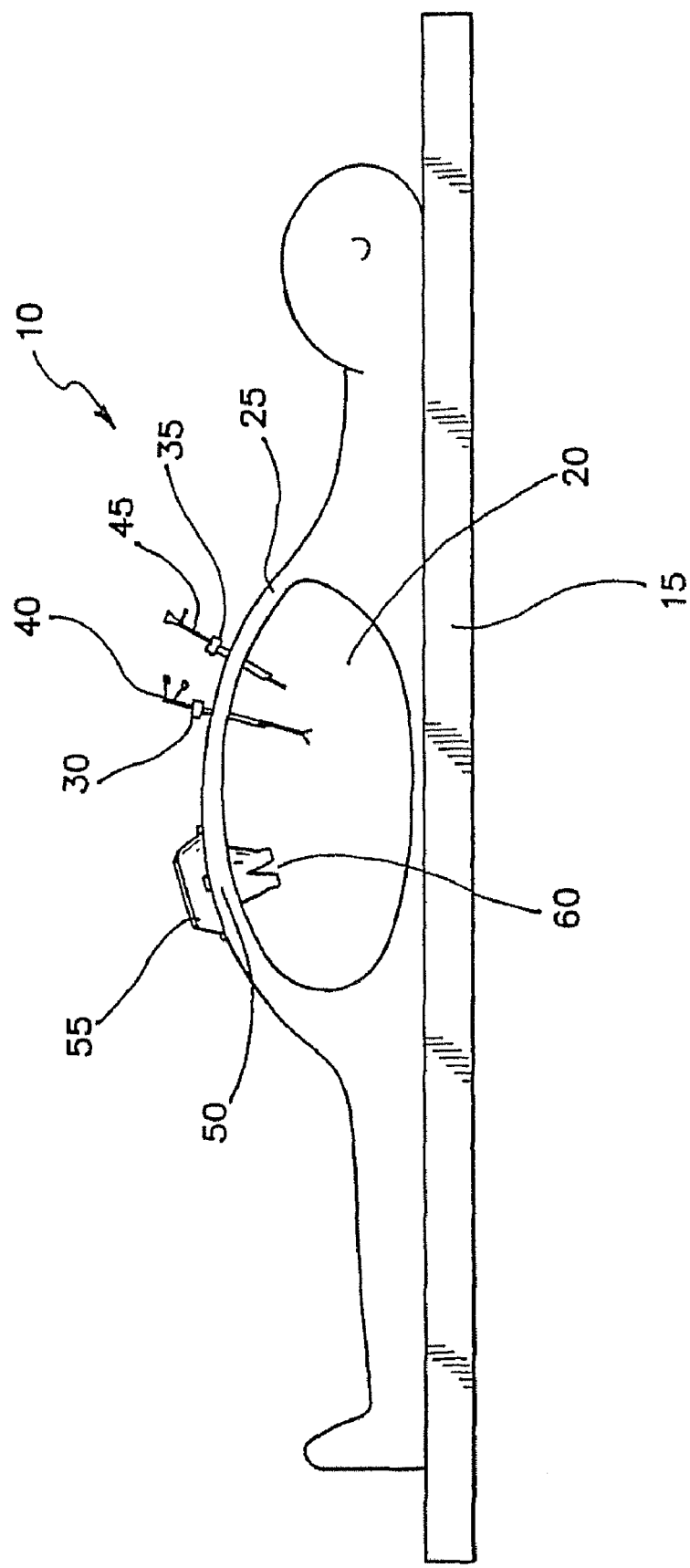
FIG. 1 is a perspective view showing a patient prone on an operating table with his abdomen insufflated, and with instrument access provided by trocars and the access device of the present invention.

A patient is illustrated in FIG. 1 and designated generally by the reference numeral 10. The patient 10 is shown in a prone position on an operating table 15, where the operative procedure is performed within an abdominal cavity 20 with instrument access provided through an abdominal wall 25. In this type of operation, commonly referred to as laparoscopic surgery, trocars 30 and 35 are commonly used to provide minimally invasive access through the abdominal wall 25 for instruments such as a grasper 40 and an endoscope 45.

Although the specific focus of this disclosure will be on a preferred laparoscopic procedure, it will be noted that laparoscopic surgery is merely representative of a type of operation wherein a procedure can be performed in a body cavity with minimal access through a body wall.

Notwithstanding the foregoing generality, it is important to note that with respect to laparoscopic surgery, it is often desirable that instruments having diameters up to 37 mm be able to insert through the abdominal wall 25 and into the abdominal cavity 20 using the same access device. This insertion of the instruments provides a surgeon with direct access to various elements of the anatomy without having to change access device or use of multiple access devices.

In order to accommodate a wide range of instruments, a small incision 50 is typically created in the abdominal wall 25. An access device 55 of the present invention can be provided to further facilitate insertion of wide instruments such as those having diameters up to about 37 mm.

Particularly in the case of laparoscopic surgery, it is advantageous to insufflate the abdominal cavity 20 with a gas, such as carbon dioxide, in order to elevate the abdominal wall 25 and thereby increase the volume of the working space within the cavity 20. Maintenance of this insufflation pressure, commonly referred to as pneumoperitoneum, is particularly difficult where access is desired across the abdominal wall 25, for example, through the trocars 30, 35, as well as the access device 55. For this reason, a substantial effort has been directed to providing such access devices with sealing characteristics both in the presence of instruments and in the absence of instruments, such as the grasper 40 and scope 45.

Were it not for the desire to maintain the pneumoperitoneum, there would be no need for the trocars 30, 35 or the access device 55. One would merely cut an incision in the abdominal wall 25 and insert the instrument directly through the incision. However, without appropriate valves or seals, the insufflation gases would merely escape through the incisions. This would be particularly detrimental in the case of the incision 50 which must be sufficiently large to accept the wide range of instruments having diameters up to 37 mm. Thus, it is a primary purpose of the access device 55 to form with the incision 50 an access or working channel 60, and to provide a valve or other sealing structure across the working channel 60 in order to maintain the pneumoperitoneum.

Figure 2:
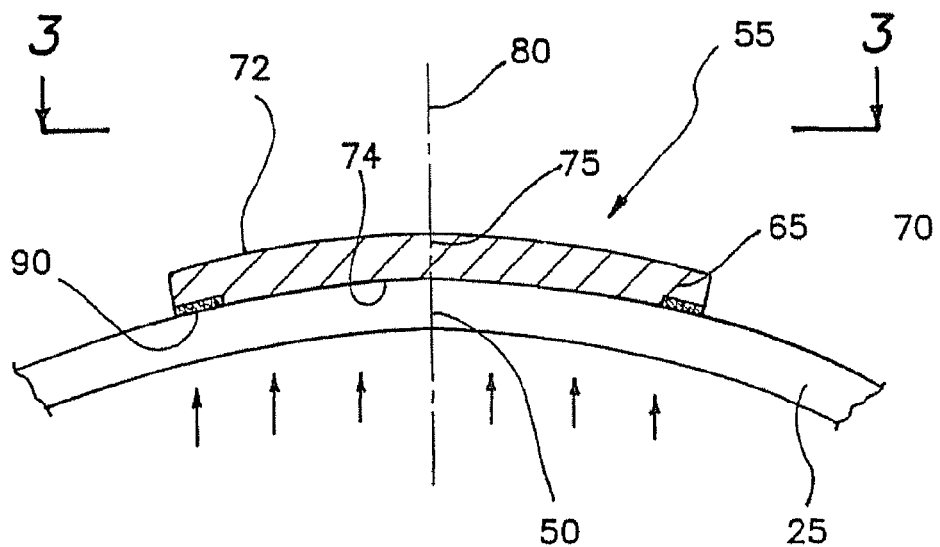
FIG. 2 is an enlarged side elevation view of the access device operatively disposed exteriorly of the abdominal wall.

An enlarged view of one embodiment of the access device 55 is illustrated in FIG. 2, which also shows the abdominal wall 25 and the incision 50. In this simple form, the access device 55 has the general configuration of a pad 65, meaning that it is generally flat and disposed in a plane such as the plane 70. Typically parallel to this plane 70 are a pair of major surfaces of 72 and 74 which provide the pad 65 with a substantial surface area. An opening or slit 75 can be formed through the pad 65, generally along an axis 80 perpendicular to the plane 70.

When operatively disposed, the opening 75 of the pad 65 is in communication with the incision 50 and, in this case, forms with the incision 50 and the working channel 60. The alignment of the opening 75 and incision 50 can occur with the pad 65 disposed exteriorly of the abdominal wall as illustrated in FIG. 2. The operative disposition of the pad 65 relative to the abdominal wall 25 requires that the pad 65 be maintained in its operative position and that it form a seal around the incision 50. Referring to the plan view of FIG. 3, these two functions are accomplished with an adhesive 85 disposed around the incision 50 between the pad 65 and the abdominal wall 25.

Figure 3:
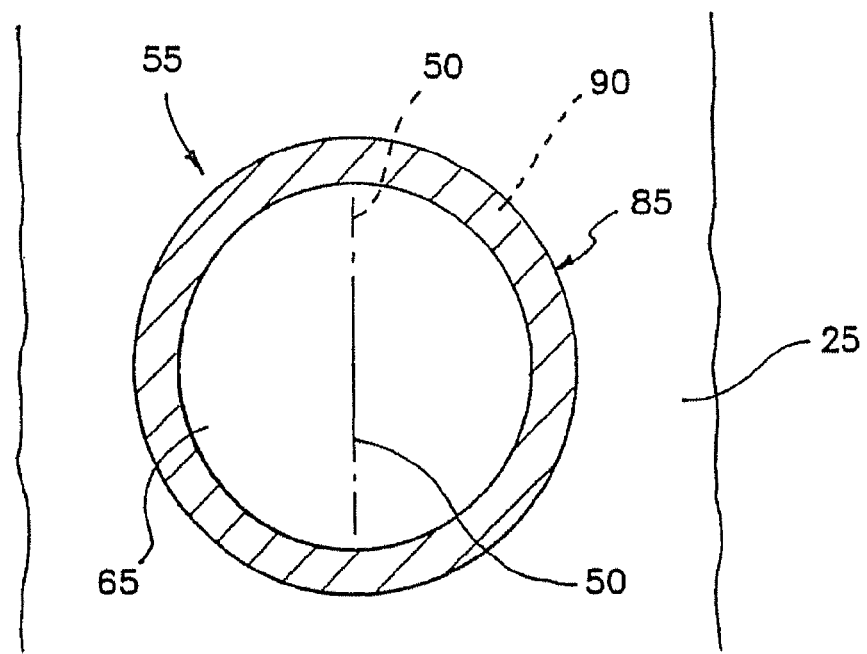
FIG. 3 is a plan view taken along lines 3-3 of FIG. 2.

If this adhesive 85 is formed as a continuous ring 90, as illustrated in FIG. 3, the pad 65 can be disposed with the ring 90 positioned circumferentially around the incision 50 to form a seal between the pad 65 and the abdominal wall 25. In the illustrated example, when the pad 65 is operatively positioned, the escape of insufflation gases is inhibited between the pad 65 and the abdominal wall 25 by the adhesive ring 90.

The escape of insufflation gases is inhibited through the opening 75 of the pad 65 by the self-sealing characteristics of the material forming the pad 65. This material of the pad 65 and its highly advantageous properties are discussed below.

It will be appreciated that the functions of the adhesive ring 90 can be accomplished in many different ways using many different materials and shapes. For example, many materials other than adhesives can be used to maintain the pad 65 in position over the incision 50. The formation of a seal around the incision 50 can also be accomplished with methods other than adhesion. Furthermore, the shape of the continuous seal formed by the adhesive 85 need not be in the shape of a circle. Rather, any continuous pattern sufficiently large to form a perimeter around the incision 50 could facilitate the desired sealing relationship.

It will be noted that whenever an instrument is inserted through the pad 65, the material of the pad conforms to the surface of the instrument and forms the instrument seal with the instrument. Accordingly, during the entire period beginning with insertion of the instrument and ending with withdrawal of the instrument, there is substantially no loss of insufflation gas through the pad 65 or any loss of pneumoperitoneum within the abdominal cavity 20.

It will be appreciated an instrument having a diameter up to 37 mm may be inserted through the access device 55 of the invention. In the absence of the instrument, the opening or slit 75 merely closes against itself to form a zero seal, thus preventing the escape of insufflation gases through the access device 55. When the instrument is inserted through the opening or slit 75, an instrument seal is formed between the material of the access device 55 and the exterior surface of the instrument. This prevents the escape of insufflation gases through the access device 55, even when an instrument is present. Thus, insufflation pressures can be maintained within the abdominal cavity 20 whether or not the instrument is in place. Note that these seals, the zero seal and the abdominal seal, can be formed as a single valve structure having properties for accommodating a full range of instrument sizes up to 37 mm in diameter.

In most cases, the single access opening 75 is used to accommodate a single instrument. It is appreciated, however, that the access device 55 can also accommodate multiple instruments of smaller diameters. That is, additional openings may be established by merely inserting the desired operative instrument through the pad 65. In this manner, the instrument can create its own access hole beside the primary opening 75. Particularly for those operative instruments having pointed distal ends, the instrument can merely be forced through the pad 65 forming its own access hole, such as the opening 75, as it is moved distally. This opening, created by the operative instrument itself, would automatically form an instrument seal as the instrument is inserted, as well as a zero seal as the instrument is withdrawn.

For operative instruments not having pointed distal ends, it is possible to form a new access hole using a secondary instrument, such as a trocar obturator. After the access hole is formed, the obturator can be removed, vacating the access hole to receive the operative instrument. Throughout this process of initially forming an access hole and ultimately inserting an operative instrument through the hole, both zero seals and instrument seals are formed to maintain the pneumoperitoneum.

With the advantages associated with (1) the formation of an instrument seal and a zero seal with a single valve accommodating a wide range of diameters, and (2) the formation of an instrument opening using the instrument itself, it will be appreciated that the concept of this invention will typically be embodied with a structure that is particularly dependent upon the material which forms the access device 55. In a preferred embodiment, the pad 65 is formed of a KRATON®/oil mixture including a KRATON® Tri-block with a Styrene-Ethylene-Butylene-Styrene (S-E-B-S) structure in combination with a mineral oil.

As described in co-pending U.S. application Ser. No. 10/381,220, filed on Mar. 20, 2003, entitled "Surgical Access Apparatus and Method," which is fully incorporated herein by reference, it can be appreciated that an almost infinite number of combinations, alloys, and Styrene to rubber ratios can be formulated, each capable of providing advantages to a particular embodiment of the invention. These advantages will typically include low durometer, high elongation, and good tear strength.

Figure 4:
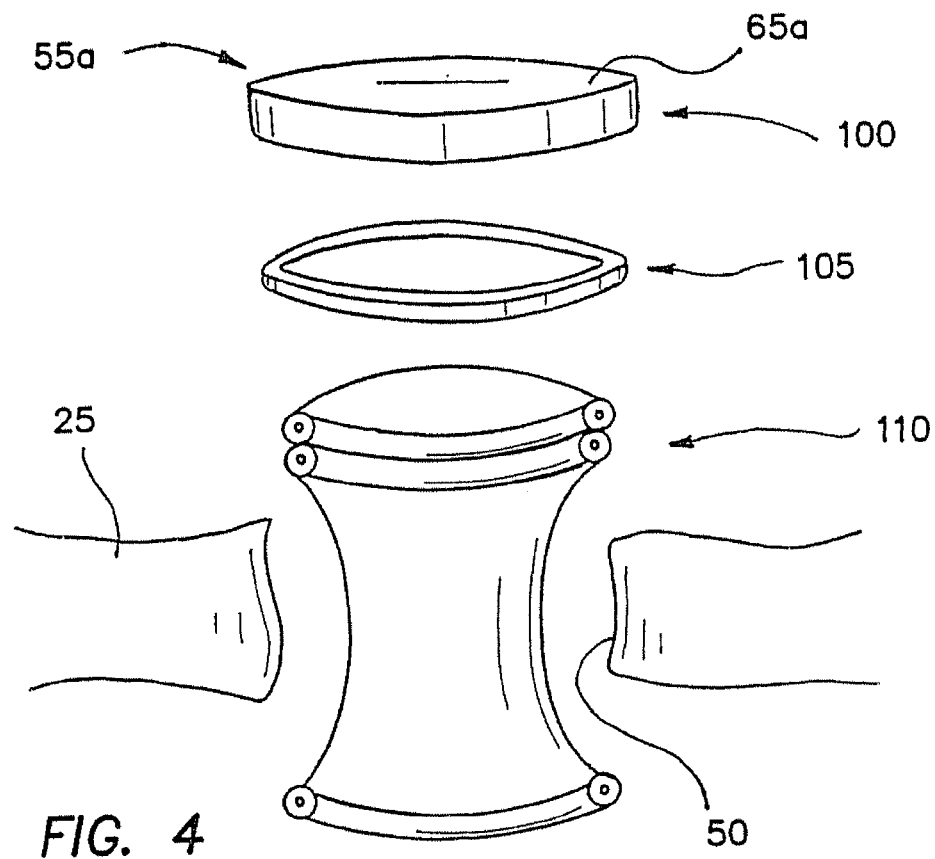
FIG. 4 is a perspective exploded view of a further embodiment including a gel cap, a base and a wound retractor.

A further embodiment of the invention is illustrated in FIG. 4 where elements of structure similar to those previously disclosed are designated with the same reference numeral followed by the lower case letter "a." This exploded view of the access device 55a includes not only the pad 65a but also a complimentary structure for maintaining the position of the pad 65a, for forming a seal between the pad 65a and the abdominal wall 25, and for dilating the incision 50 to a variable extent as required by a surgeon. In this case, the access device 55a includes three components, a gel cap 100, base 105, and a wound retractor 110 as described in co-pending International Application No. PCT/US03/17389, filed on Jun. 3, 2003, entitled "Wound Retractor," which is fully incorporated herein by reference.

Figure 6:
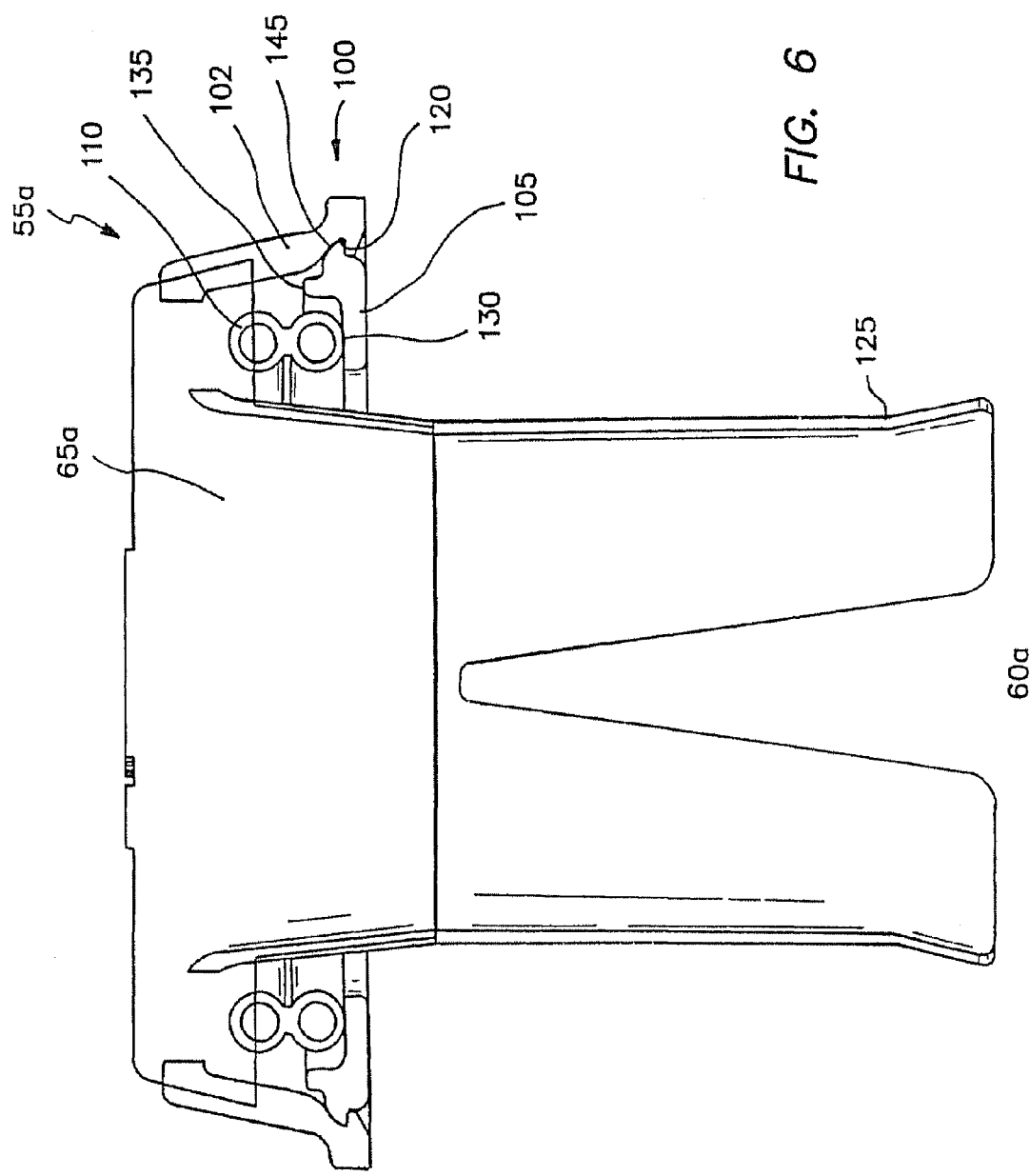
FIG. 6 is a cross-section view of an access device of the invention including a gel cap, a base, a wound retractor, and a protective sleeve formed around an inner diameter of a cap ring of the gel cap.
Figure 7:
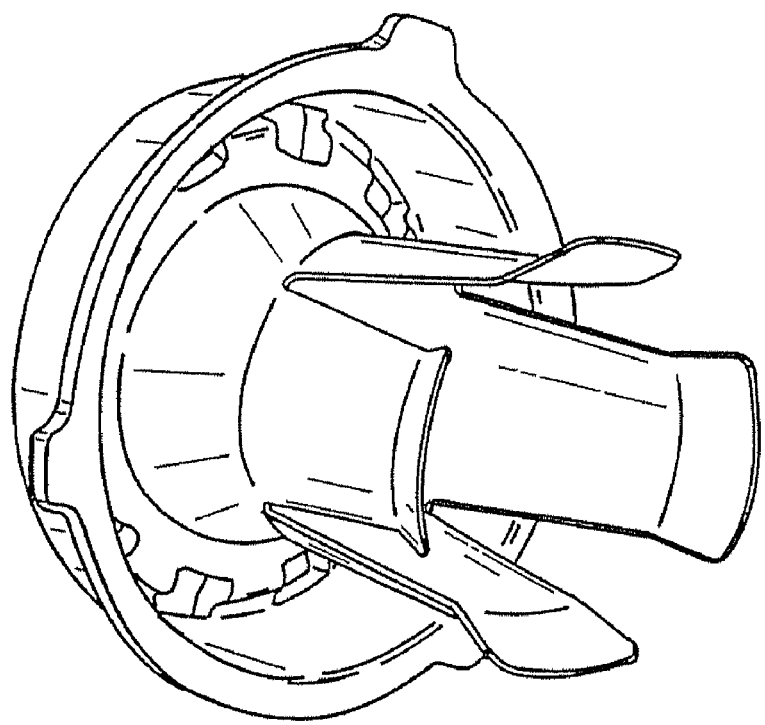
FIG. 7 is a three-dimensional view of the protective sleeve formed around the inner diameter of the cap ring of the access device of the invention.
Figure 8:
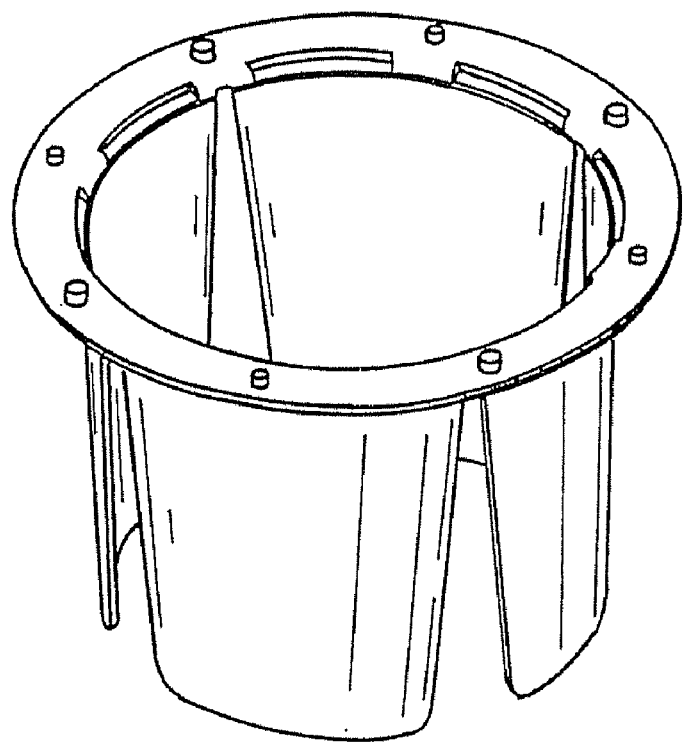
FIG. 8 is a three-dimensional view of a protective sleeve formed around an inner diameter of a cap ring of an access device in accordance to another embodiment of the invention.

Referring to FIG. 6, there is shown a cross-sectional view of the access device 55a, with the gel cap 100 and the base 105 attached together and the wound retractor 110 held therein. The gel cap 100 further includes a circumferential cap ring 102, which can be inserted and molded to the pad 65a, and a protective shield or sleeve 125, which can be bonded or molded into cap 100. The shield or sleeve 125 is positioned under pad 65a and circumferentially around an inner diameter of cap ring 102, and is directed into the incision 50. The shield or sleeve 125 operates to protect the sheath of wound retractor 110 from sharp instruments as the instruments are inserted and withdrawn through the pad 65a; the shield 125 also operates to direct instruments through the pad 65a. The shield 125 may be a single tubular member or it may comprise a plurality of axially extending sleeve members having a plurality of axial slits as illustrated in FIGS. 7 and 8. The shield 125 may comprise of the same or different materials as the cap ring 102. The resulting gel cap 100 forms a seal with the base 105, thereby defining a working channel 60a through the pad 65a, the cap ring 102, the base 105, and the wound retractor 110. In the manner previously discussed, this working channel 60a includes the single valve formed by the gel pad 65a which provides both a zero seal and an instrument seal for a wide range of instrument diameters.

Figure 5:
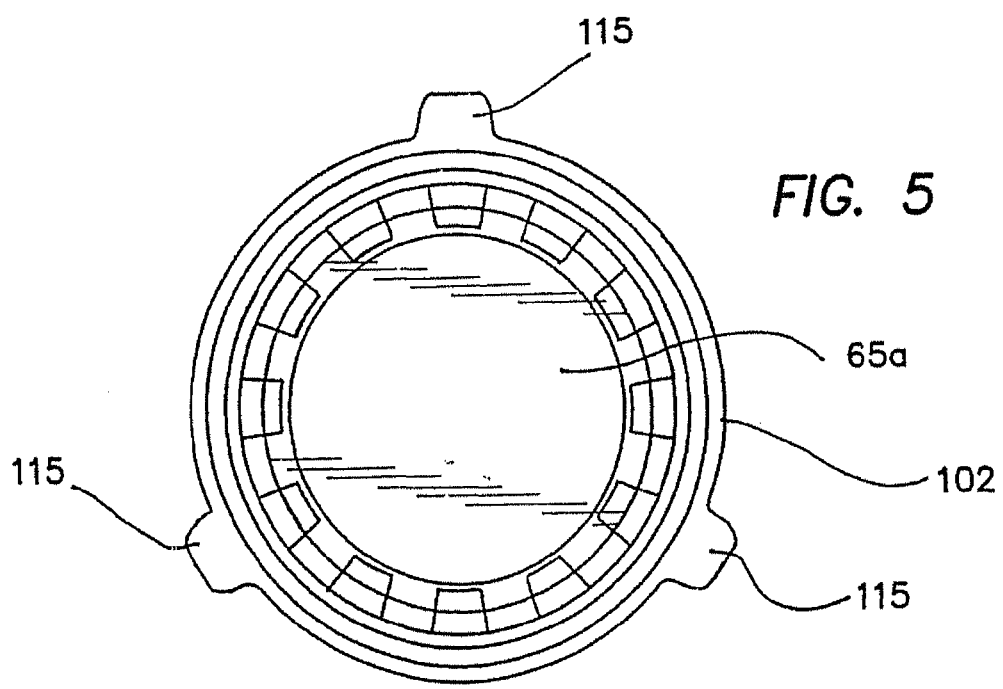
FIG. 5 is a top plan view of a gel cap of an access device of the invention.

The structure associated with the gel cap 100 is described in greater detail with reference to FIG. 5. In the top plan view of FIG. 5, it can be seen that this embodiment includes the gel pad 65a centrally disposed within the circumferential cap ring 102. Holding tabs 115 can be provided to extend radially outwardly of the cap ring 102. These holding tabs 115 can facilitate the sealing engagement of the gel cap 100 with the base 105 in the manner described in greater detail below.

The gel pad 65a can be formed of any of the materials previously discussed although the preferred embodiment includes the KRATON©/mineral oil gel. The cap ring 102 for such an embodiment can be advantageously formed of KRATON® only. This will make the cap ring 102 more rigid than the gel pad 65a while maintaining an excellent material interface between the pad 65a and the ring 102. In a typical manufacturing operation, the cap ring 102 will be pre-disposed in the mold for the gel pad 65a with the unitary structure of the gel cap 100 resulting.

Figure 9:
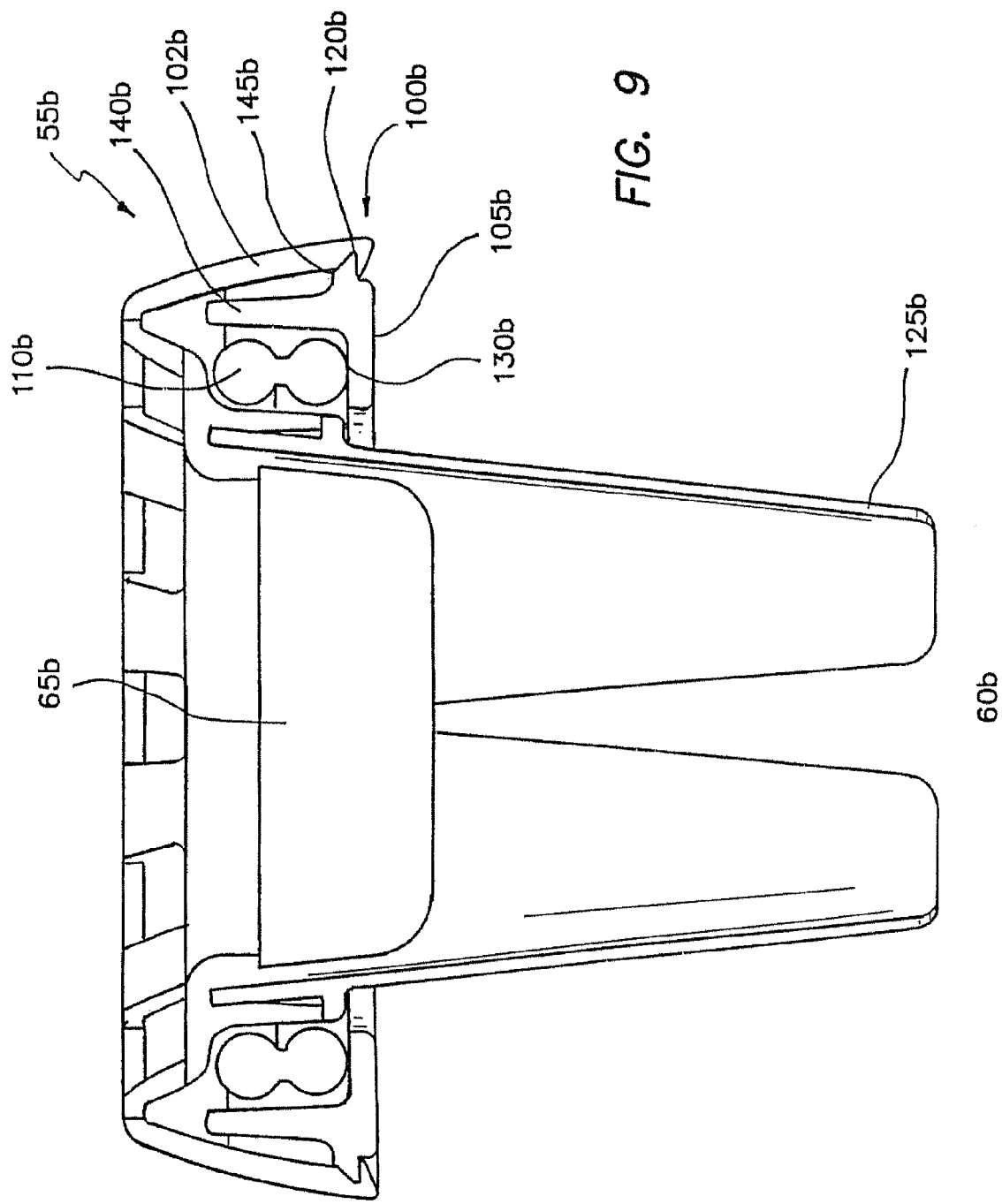
FIG. 9 is a cross-section view of an access device in accordance with another embodiment of the invention including a gel cap, a base, a wound retractor, and a protective sleeve formed around an inner diameter of a cap ring of the gel cap.
Figure 10:
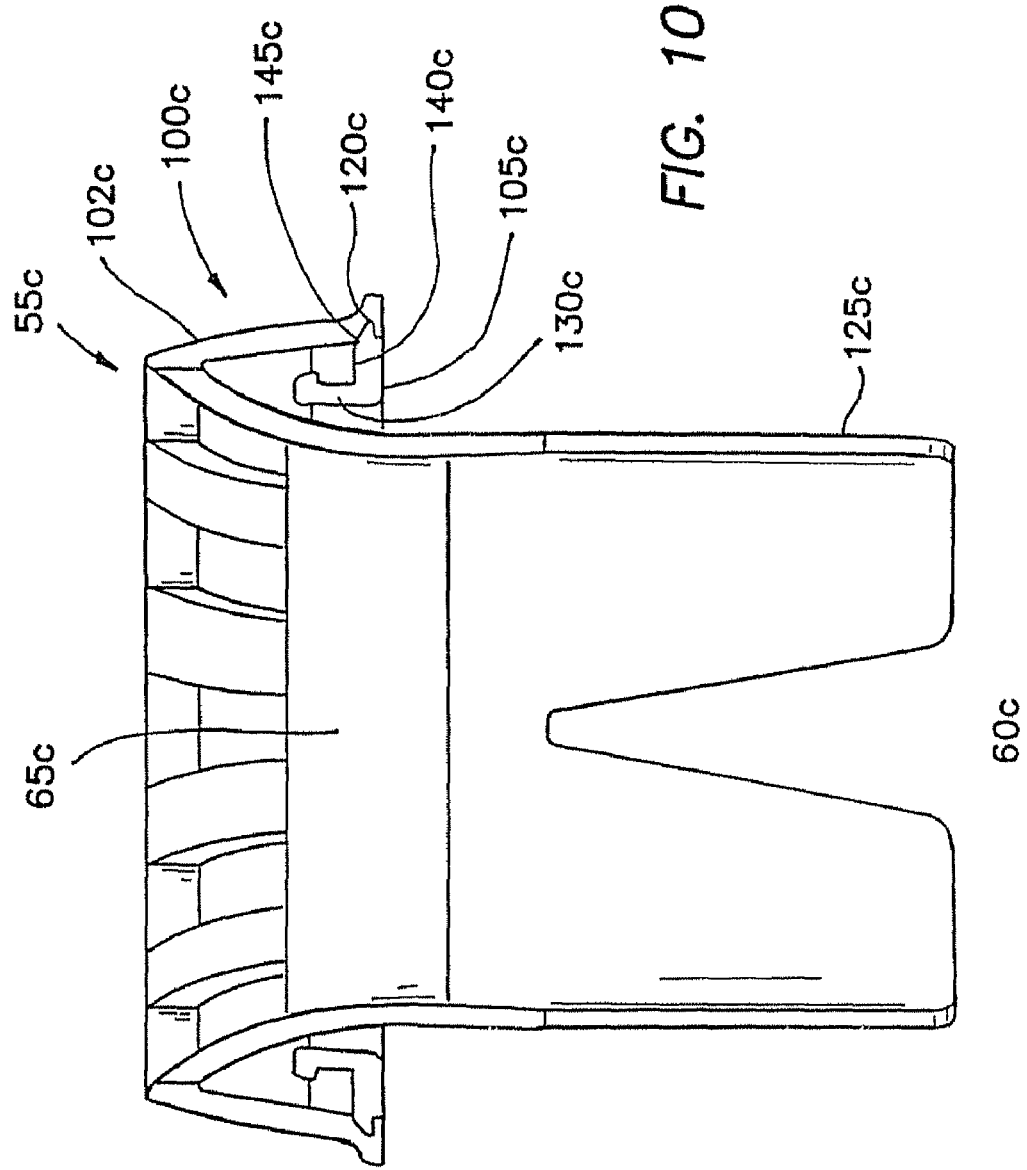
FIG. 10 is a cross-section view of an access device in accordance with another embodiment of the invention including a gel cap, a base, a wound retractor (not shown), and a protective sleeve formed around an inner diameter of a cap ring of the gel cap.

The cross-section view of FIG. 6 further illustrates an annular void 120 formed on the inner circumference of the cap ring 102. This void 120 is of particular advantage in forming a sealing relationship with the base 105 in the manner discussed in greater detail below. FIGS. 9 and 10 illustrate additional exemplary embodiments of the invention having modifications that could be made to the gel cap 100 and/or the base 105 so that the access device 55 can be used with the wound retractor 110. Referring back to FIG. 6, it will be noted that the base 105 can be provided with a generally straight inner surface 130 which extends distally to a rounded end surface 135 and outwardly from the end surface 135 along an annular lip 145, which is sized and configured to fit into the annular void 120 formed on the inner circumference of cap ring 102.

In another embodiment of the invention, FIG. 9 illustrates a base 105b having a generally straight inner surface 130b which extends distally to a raised wall 140b and outwardly from the raised wall 140b along an annular lip 145b, which is sized and configured to fit into an annular void 120b formed on the inner circumference of a corresponding cap ring 102b. In yet another embodiment of the invention, FIG. 10 illustrates a base 105c having a raised wall 130c along an inner diameter and a generally straight surface 140c extending distally along an annular lip 145c, which is sized and configured to fit into an annular void 120c formed on the inner circumference of a corresponding cap ring 102c.

Figure 11:
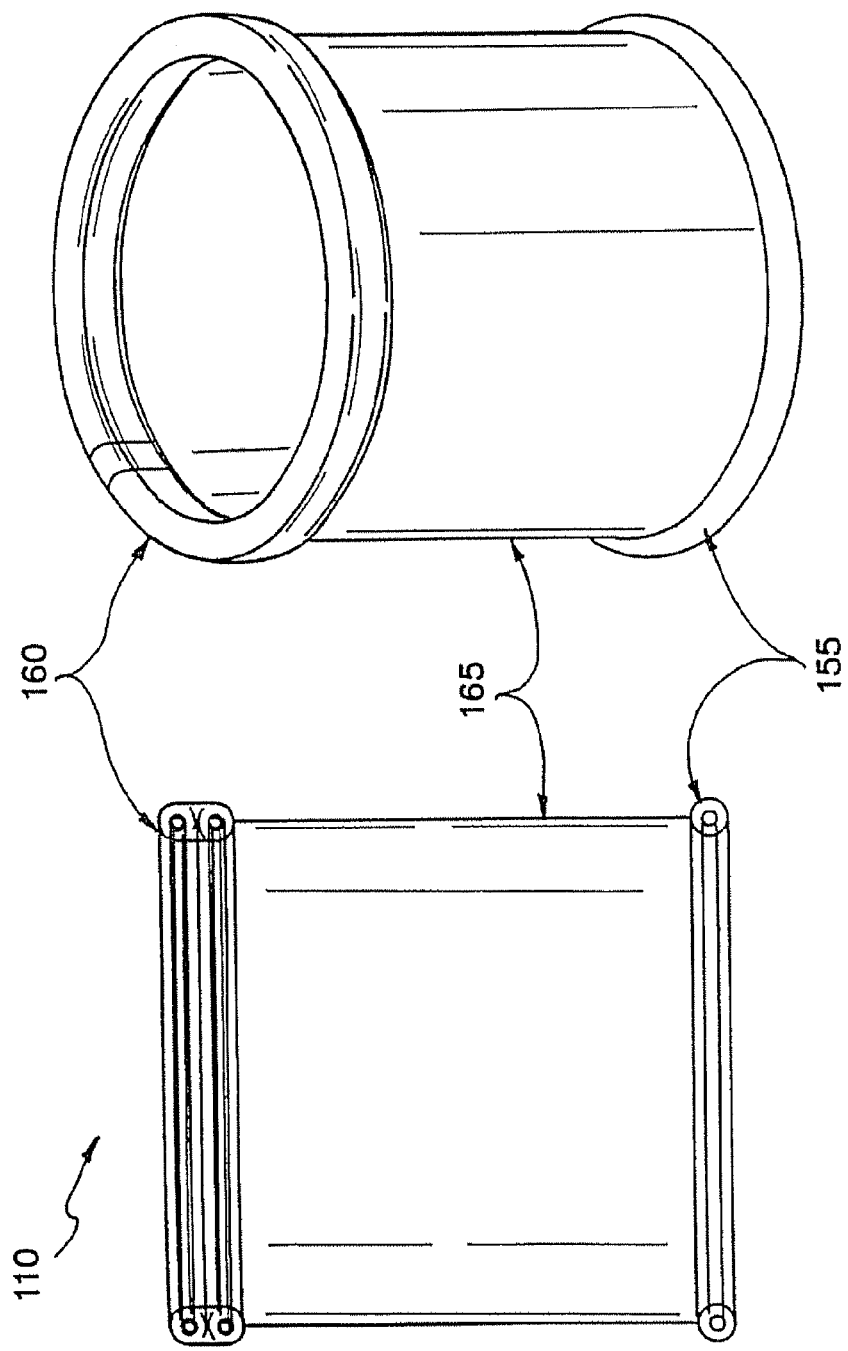
FIG. 11 illustrates a cross-section view and a three-dimensional view of the wound retractor of an access device of the invention including an inner ring, an outer ring, and a flexible sleeve.

Referring to FIG. 11, there is shown the incrementally adjustable wound retractor 110 of the invention which operates to seal edges of a surgical incision and forms an opening in a patient's body cavity. The wound retractor 110 comprises an inner ring 155, an outer ring 160, and a flexible sleeve 165 connecting the inner ring 155 and the outer ring 160. The wound retractor 110 provides a path for a surgeon to insert instruments through the opening formed by the wound retractor 110. The wound retractor 110 is incrementally adjustable to fit a wide range of incision sizes. The wound retractor 110 is installed or placed in a body cavity such that the inner and outer rings 155, 160 expand around inner and outer edges of the incision. Any portion of the flexible sleeve 165 extending outside the incision can be easily rolled onto the outer ring 160 to tightly seal the sides of the wound. The outer ring 160 is preferably shaped to provide audible and/or tactile feedback to the user. The outer ring 160 includes surfaces that are easy to grip and turn to allow the user to manually turn the outer ring 160 and roll up the flexible sleeve 165 with ease. The outer ring 160 may be solid or include a single or multiple lumen(s) with rod(s) placed therein to provide audible signal to the user as the outer ring 160 is turned.

Figure 12:
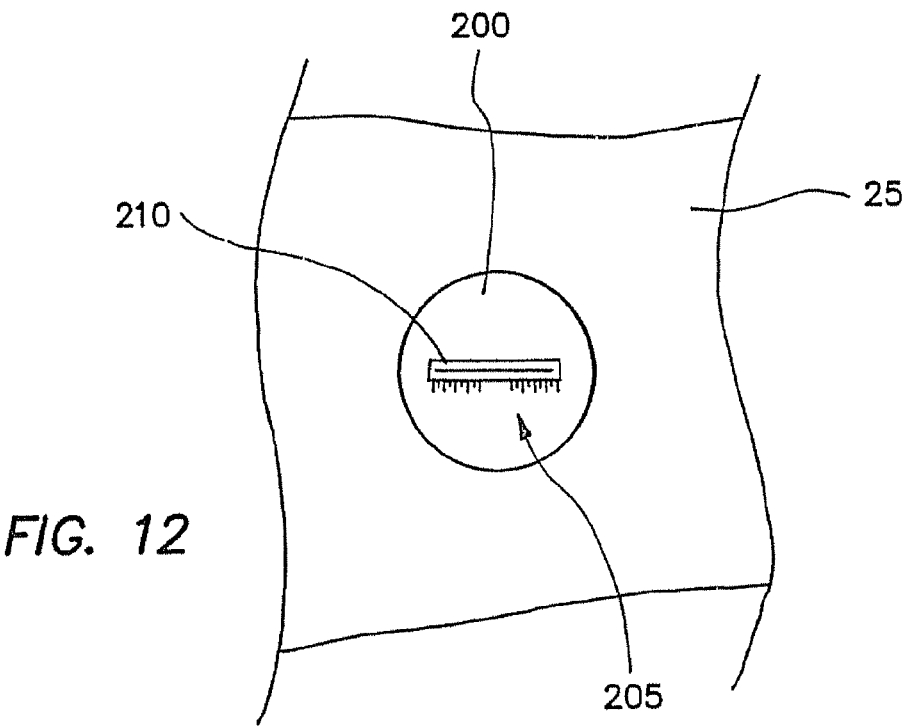
FIG. 12 is a top plan view showing use of a template.
Figure 13:
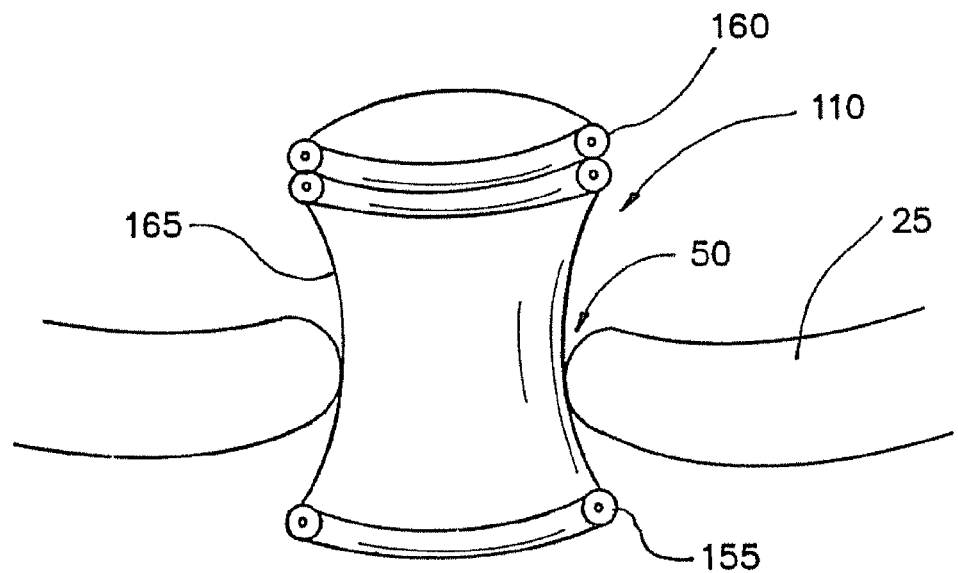
FIG. 13 is an axial cross-section view showing placement of the inner ring and securement of the flexible sleeve of the wound retractor of the invention.

The method of using the access device of the present invention is illustrated in the progressive use of FIGS. 12 and 13. In FIG. 12, a top plan view of the abdominal wall 25 of the patient 10 is illustrated with a template 200 positioned to facilitate location of the incision 50. The size of the incision 50 can be determined with the indicia 205 on the template 200 showing the lengths of the incision. After the incision 50 has been cut along the line 210, the template 200 can be removed. As illustrated in FIG. 13, the wound retractor 110 can then be mounted through the incision 50. Initially the inner ring 155 is compressed and fed through the incision 50. On the inner surface of the abdominal wall 25, the inner ring 155 is free to expand to its larger diameter. Any portion of the flexible sleeve 165 extending outside the incision 50 can be easily rolled onto the outer ring 160 to tightly seal the sides of the wound. As noted, when the sleeve 165 is axially stretched, it will create radial forces on the abdominal wall 25 which will tend to enlarge the incision 50. The greater the axial stretch, the larger the incision 50.

A final step remaining in this process is the attachment of the gel cap 100 to the base 105. This is accomplished as illustrated in FIGS. 6, 9 and 10 by capturing the annular lip 145 of the base 105 in the annular void 120 of the gel cap 100. Bending the holding tabs 115 upwardly and outwardly facilitates this engagement which ultimately forms a seal between the base 105 and the gel cap 100.

Although this invention has been disclosed with reference to certain structural configurations, it will be appreciated that these products are merely representative of many different embodiments of the invention. Accordingly, one is cautioned not to limit the concept only to the disclosed embodiments, but rather encouraged to determine the scope of the invention only with reference to the following claims.

The invention claimed is:

1. A surgical access device facilitating a sealing relationship with a surgical instrument extending through the device and into patient, the surgical access device comprising:
a retractor having a proximal end and a distal end with a flexible sleeve extending between the proximal end and the distal end and defining an access channel extending into a patient;
a valve structure arranged to be coupled to the retractor and sealing the proximal end of the retractor and the access channel into the patient; and
a protective shield having a nonadjustable length and the flexible sleeve of the retractor having an adjustable length, the protective shield being positioned between the valve structure and the retractor;
wherein the valve structure comprises a gel material including an elastomer and a cap ring surrounding the gel material.

2. The device of claim 1 wherein the protective shield is coupled to the valve structure.

3. The device of claim 1 wherein the protective shield is a plurality of axially extending shield members with an axial slit separating each of the plurality of axially extending shield members.

4. The device of claim 1 wherein the protective shield provides for wound protection during insertion and withdrawal of the instrument.

5. The device of claim 1 wherein the protective shield is a single tubular member.

6. A surgical access device facilitating a sealing relationship with a surgical instrument extending through the device and into patient, the surgical access device, comprising:
a valve structure disposed relative to an incision in a sealing relationship with a body wall around the incision and extending into communication with the incision in the patient;
a valve included in the valve structure and disposed relative to the incision in the body wall, the valve having a seal;
a cap ring surrounding the seal forming a zero seal in the absence of the instrument extending through the seal and forming a seal with the instrument in the presence of the instrument extending through the seal;
a protective shield positioned circumferentially around an inner diameter of the cap ring and extendable into the patient, the protective shield having a proximal end with a decreasing taper to a middle portion of the protective shield and having a distal end with an increasing tapered from and away from the middle portion of the protective shield and the protective shield having a fixed nonadjustable length; and a retractor having a proximal end and a distal end with a flexible sleeve extending between the proximal end and the distal end;
wherein the retractor is arranged to be coupled to the cap ring and the protective shield is positioned adjacent to the retractor and the cap ring is coupled to the valve.

7. The device of claim 6 wherein the inner diameter of the cap ring is larger than a diameter of the distal end of the protective shield.

8. The device of claim 6 wherein the protective shield comprises a plurality of axially extending shield members.

9. The device of claim 6 wherein the protective shield provides for wound protection during insertion and withdrawal of the instrument.

10. The device of claim 6 wherein the protective shield is a single tubular member.

11. The device of claim 6 wherein the protective shield is coupled to the cap ring.

12. The device of claim 6 wherein the seal is made of gel material sealing the proximal end of the retractor.

* * * * *